(12) United States Patent
Zhang et al.

(10) Patent No.: US 12,070,702 B2
(45) Date of Patent: Aug. 27, 2024

(54) ANION EXCHANGE CHROMATOGRAPHY FOR RECOMBINANT AAV PRODUCTION

(71) Applicant: REGENXBIO INC., Rockville, MD (US)

(72) Inventors: Claire G. Zhang, Rockville, MD (US); Jeffrey Levine, Rockville, MD (US); Sara Zafar, Rockville, MD (US); Franz M. Gerner, Rockville, MD (US)

(73) Assignee: REGENXBIO INC., Rockville, MD (US)

( * ) Notice: Subject to any disclaimer, the term of this patent is extended or adjusted under 35 U.S.C. 154(b) by 926 days.

(21) Appl. No.: 17/251,869

(22) PCT Filed: Jun. 13, 2019

(86) PCT No.: PCT/US2019/037013
§ 371 (c)(1),
(2) Date: Dec. 14, 2020

(87) PCT Pub. No.: WO2019/241535
PCT Pub. Date: Dec. 19, 2019

(65) Prior Publication Data
US 2021/0370199 A1 Dec. 2, 2021

Related U.S. Application Data

(60) Provisional application No. 62/684,835, filed on Jun. 14, 2018.

(51) Int. Cl.
*C12N 7/00* (2006.01)
*B01D 15/16* (2006.01)
*B01D 15/36* (2006.01)

(52) U.S. Cl.
CPC ......... *B01D 15/363* (2013.01); *B01D 15/166* (2013.01); *C12N 7/00* (2013.01); *C12N 2750/14123* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 6,664,305 B2 | 12/2003 | Jungbauer et al. | |
| 2003/0125204 A1 | 7/2003 | Jungbauer et al. | |
| 2017/0260545 A1 | 9/2017 | Qu et al. | |
| 2019/0002841 A1 | 1/2019 | Lock et al. | |
| 2019/0002842 A1 | 1/2019 | Lock et al. | |
| 2019/0002844 A1 | 1/2019 | Lock et al. | |

FOREIGN PATENT DOCUMENTS

| | | | | |
|---|---|---|---|---|
| WO | 0148155 A2 | 7/2001 | | |
| WO | 0212455 A1 | 2/2002 | | |
| WO | 2017/100674 | 6/2017 | | |
| WO | 2017/100676 | 6/2017 | | |
| WO | 2017/100704 | 6/2017 | | |
| WO | WO 2017/100676 | * 6/2017 | ............ | C12N 12/00 |
| WO | 2017/160360 | 9/2017 | | |
| WO | 2019/178495 | 9/2019 | | |

OTHER PUBLICATIONS

M. Leskovec et al., "An Industrial Purification Platform for AAV", BIA Separations d.o.o., Mirce 21, 5270 Ajdovščina, Slovenia, 1 page.
Lidija Urbas et al., "Monolithic Columns for Purification and Inprocess Control of Viruses and Virus-like Particles", Engineering Conferences International ECI Digital Archives, Vaccine Technology IV Proceedings, Spring May 24, 2012, 18 pages.
Unknown, "A048 Chromatographic separation of full and empty AAV8 capsids", BIA Separations, accessed at https://www.biaseparations.com/en/library/application-notes?tag=viruses, 2015, 2 pages.
International Search Report and Written Opinion of the ISA for PCT/US2019/037013, mailed Dec. 11, 2019, 18 pgs.
Flotte et al., "Phase 2 clinical trial of a recombinant adenoassociated viral vector expressing α1-antitrypsin: interim results," Hum Gene Ther. 22(10):1239-47 (2011).
Lock, M., et al., "Analysis of Particle Content of Recombinant Adeno-Associated Virus Serotype 8 Vectors by Ion-Exchange Chromatography," Human Gene Therapy Methods: Part B 23:56-64 (Feb. 2012).
Oksanen et al., "Monolithicionexchangechromatographicmethodsforviruspurification," Virology, 434: 271-277 (2012).
Sekirnik at al., "Chromatographic separation of full and empty AAV8 capsids," accessed at https://www.biaseparations.com/en/library/posters/926/chromatographic-separation-of-full-and-empty-aav8-capsids on May 30, 2018.
Unknown, "A022 Rapid, Single-step Purification Method for Adenovirus Vectors Using CIM® QA Disk Monolithic Column," accessed at https://www.biaseparations.com/en/library/application-notes/27/rapid-single-step-purification-method-for-adenovirus-vectors-using-cimr-qa-disk-monolithic-column; Feb. 2010.
Unknown, "A041 Chromatographic separation of full and empty Adeno-Associated Virus (AAV) particles on CIM® monoliths," accessed at https://www.biaseparations.com/en/library/application-notes/832/chromatographic-separation-of-full-and-empty-adeno-associated-virus-aav-particles-on-cimr-monoliths; 2015.
Unknown, "A048 Chromatographic separation of full and empty AAV8 capsids," accessed on at https://www.biaseparations.com/en/library/posters/926/chromatographic-separation-of-full-and-empty-aav8-capsids; 2015.

* cited by examiner

*Primary Examiner* — Agnieszka Boesen
(74) *Attorney, Agent, or Firm* — NIXON & VANDERHYE, PC

(57) ABSTRACT

Provided herein are methods for the purification of recombinant Adeno-Associated Virus (rAAV) particles using anion exchange chromatography.

13 Claims, 19 Drawing Sheets

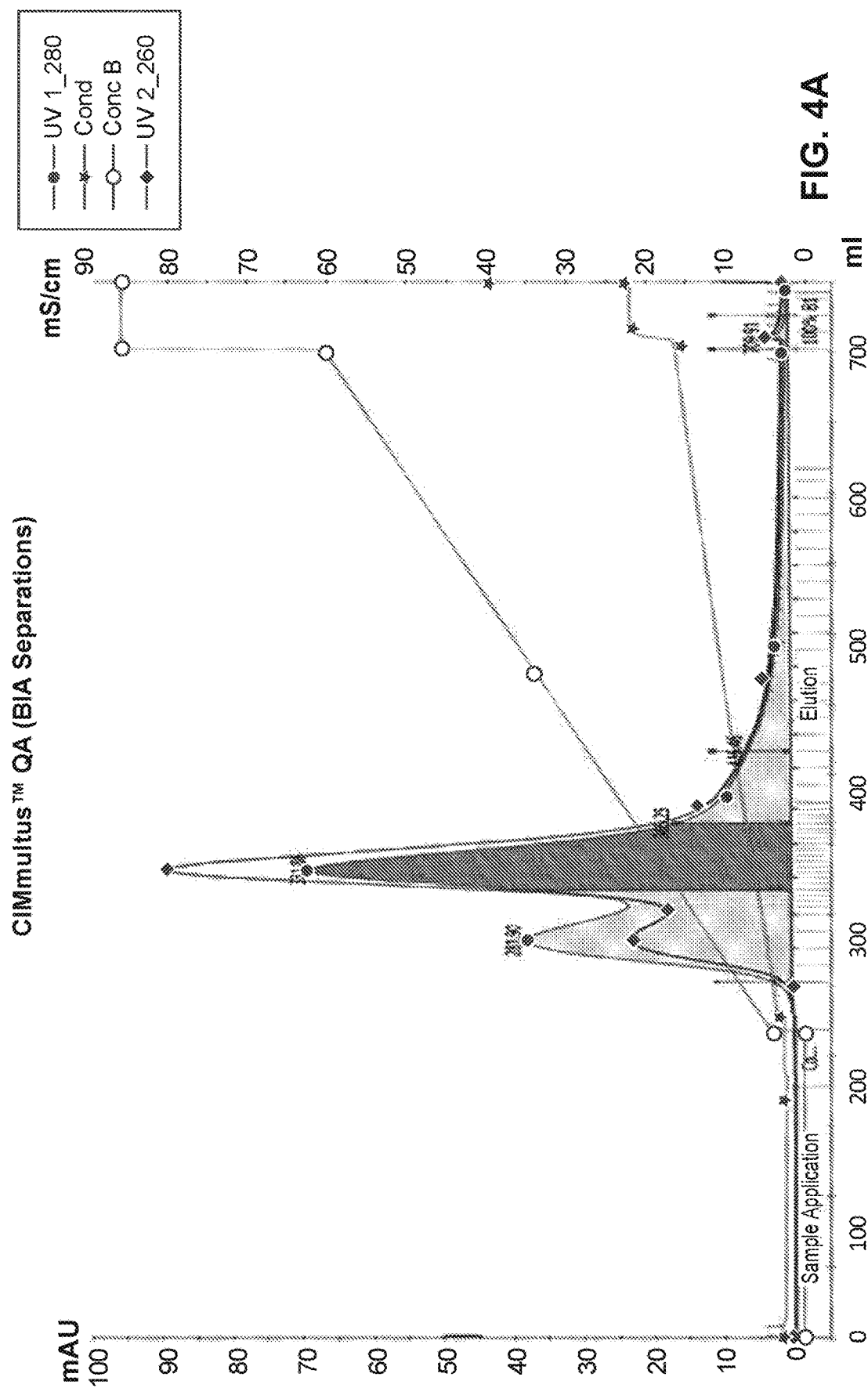

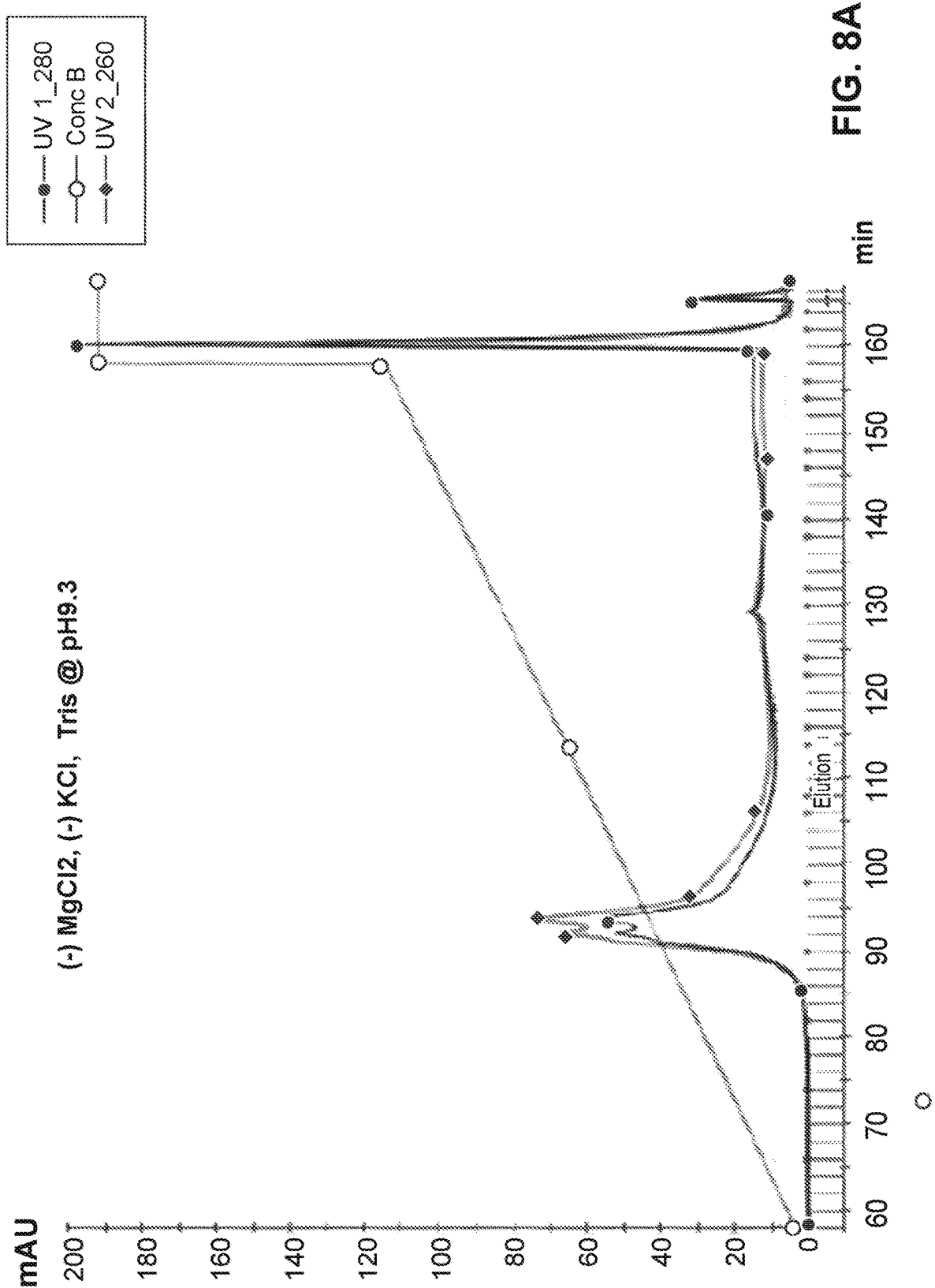

ANION EXCHANGE CHROMATOGRAPHY FOR RECOMBINANT AAV PRODUCTION

CROSS-REFERENCE TO RELATED APPLICATIONS

This application is the U.S. national phase of International Application No. PCT/US2019/037013 filed Jun. 13, 2019 which designated the U.S. and claims the benefit of priority of U.S. Provisional Application No. 62/684,835 filed Jun. 14, 2018, the entire content of which is incorporated herein in its entirety.

BACKGROUND

Recombinant Adeno-Associated Virus (AAV)-based vectors are currently the most widely used gene therapy products in development. The preferred use of rAAV vector systems is due, in part, to the lack of disease associated with the wild-type virus, the ability of AAV to transduce non-dividing as well as dividing cells, and the resulting long-term robust transgene expression observed in clinical trials and that indicate great potential for delivery in gene therapy indications. Additionally, different naturally occurring and recombinant rAAV vector serotypes, specifically target different tissues, organs, and cells, and help evade any pre-existing immunity to the vector, thus expanding the therapeutic applications of AAV-based gene therapies.

However, before AAV based gene therapies can be more widely adopted for late clinical stage and commercial use, new methods for large scale GMP compliant purification of functional rAAV particles need to be developed. One challenge facing research and development personnel for downstream processing of viral vectors is ensuring an efficient separation of the functional viral particles from contaminating, closely related molecular species, such as inactive vector forms including empty and partially filled viral capsids (product-related impurities), helper virus, and cell membrane vesicles. Given the structural surface similarity the product-related impurities (e.g., empty and partially filled capsids) share with functional rAAV particles, removal of these contaminants poses a significant challenge as these contaminants are difficult, and sometimes impossible, to separate using currently described purification procedures. The removal of product-related impurities is critically important because the presence of empty and partially filled capsids in a therapeutic composition increases the amount of potentially immunogenic capsid proteins in a single unit dose, which is designed to deliver a pre-set number of transgene copies. By reducing the empty and partially filled capsids in a composition, a unit dose of transgene copies can be delivered with a smaller amount of capsid proteins, thereby reducing the chance that a patient develops adverse immune reactions to the AAV particles. Thus, there is a need for GMP compliant processes to isolate rAAV particles.

BRIEF SUMMARY

In one aspect, the disclosure provides methods for isolating recombinant AAV (rAAV) particles from a feed composition (e.g., the eluate of an rAAV affinity chromatography column) comprising rAAV particles and an impurity (e.g., empty/partially filled viral capsid or an viral aggregate) by contacting the composition with a anion exchange chromatography resin (e.g. monolith anion exchange chromatography resin or AEX resin comprising a quaternary amine ligand) and recovering a product composition comprising the isolated rAAV particles.

In another aspect, the disclosure provides methods for improving the separation between empty or partially filled recombinant adeno-associated virus (rAAV) particles and full rAAV particles during anion exchange chromatography by contacting a feed composition containing empty, partially filled and full rAAV particles with an anion exchange chromatography resin (e.g., AEX resin comprising a quaternary amine ligand) and recovering a product composition comprising the isolated rAAV particles.

In another aspect, the disclosure provides methods for improving the separation between improving the separation between recombinant adeno-associated virus (rAAV) particles and viral aggregates during anion exchange chromatography by contacting a feed composition containing rAAV particles and viral aggregates with an anion exchange chromatography resin (e.g., AEX resin comprising a quaternary amine ligand) and recovering a product composition comprising the isolated rAAV particles.

In some embodiments, the methods disclosed herein encompass generating the feed composition by a method comprising upstream processing such as, for example, harvest of a cell culture, clarification of the harvested cell culture (e.g., by centrifugation or depth filtration), cell supernatant of an adherent cell culture, tangential flow filtration, affinity chromatography, cation exchange chromatography, size exclusion chromatography, hydrophobic interaction chromatography, sterile filtration, or any combination(s) thereof. In some embodiments, the upstream processing does not include centrifugation. In some embodiments, the methods disclosed herein further encompass processing the product composition by downstream processing steps such as, for example, tangential flow filtration, cation exchange chromatography, hydrophobic interaction chromatography, size exclusion chromatography, and/or sterile filtration, or any combination(s) thereof. In further embodiments, the methods include upstream processing and downstream processing. The upstream and/or downstream processing may be used alone or in various combinations. In some embodiments, a method disclosed herein comprises harvest of a cell culture or cell culture supernatant, clarification of the harvested cell culture by depth filtration, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method disclosed herein comprises harvest of a cell culture, clarification of the harvested cell culture or cell culture supernatant, by depth filtration, a first sterile filtration, affinity chromatography, anion exchange chromatography (e.g., monolith anion exchange chromatography or AEX chromatography using a quaternary amine ligand), tangential flow filtration, and a second sterile filtration. In some embodiments, a method disclosed herein comprises clarification of a harvested cell culture or cell culture supernatant by depth filtration, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method disclosed herein comprises clarification of a harvested cell culture or cell culture supernatant by depth filtration, a first sterile filtration, affinity chromatography, anion exchange chromatography (e.g., monolith anion exchange chromatography or AEX chromatography using a quaternary amine ligand), tangential flow filtration, and a second sterile filtration.

In some embodiments, the disclosure provides:

[1.] A method for isolating recombinant adeno-associated virus (rAAV) particles from a feed composition containing rAAV particles and an impurity comprising:
  (a) contacting the feed composition with an anion exchange chromatography media under conditions that allow binding of the rAAV particles to the chromatography media;
  (b) eluting the rAAV particles from the chromatography media using a linear gradient; and
  (c) recovering an eluate comprising the eluted rAAV particles;
wherein
  (i) the impurity comprises an empty viral capsid, partially filled viral capsid, and/or a viral aggregate, and
  (ii) the method is characterized by one or more of:
    a. the feed composition has a $Mg^{2+}$ concentration of between about 0.1 mM and about 20 mM,
    b. the feed composition has a $K^+$ concentration of between about 0.1 mM and about 20 mM,
    c. the feed composition has a pH of between about 6.5 and about 10.5,
    d. the eluting is done at a flow rate of between 0.1 CV/min and 5 CV/min, and
    e. the linear salt gradient comprises a volume of between about 5 and about 100 CV.

[2.] The method of [1], wherein the method is characterized by two or more of:
  a. the feed composition has a $Mg^{2+}$ concentration of between about 0.1 mM and about 20 mM,
  b. the feed composition has a $K^+$ concentration of between about 0.1 mM and about 20 mM,
  c. the feed composition has a pH of between about 6.5 and about 10.5,
  d. the eluting is done at a flow rate of between 0.1 CV/min and 5 CV/min, and
  e. the linear salt gradient comprises a volume of between about 5 and about 100 CV.

[3.] The method of [1], wherein the method is characterized by that
  a. the feed composition has a $Mg^{2+}$ concentration of between about 0.1 mM and about 20 mM,
  b. the feed composition has a $K^+$ concentration of between about 0.1 mM and about 20 mM, and
  c. the feed composition has a pH of between about 6.5 and about 10.5.

[4.] The method of [1], wherein the method is characterized by that
  a. the feed composition has a $Mg^{2+}$ concentration of between about 0.1 mM and about 20 mM,
  b. the feed composition has a $K^+$ concentration of between about 0.1 mM and about 20 mM,
  c. the feed composition has a pH of between about 6.5 and about 10.5,
  d. the eluting is done at a flow rate of between 0.1 CV/min and 5 CV/min, and
  e. the linear salt gradient comprises a volume of between about 5 and about 100 CV.

[5.] The method of any one of [1] to [4], wherein
  a. the feed composition has a $Mg^{2+}$ concentration of between about 0.5 mM and about 10 mM,
  b. the feed composition has a $K^+$ concentration of between about 0.5 mM and about 10 mM,
  c. the feed composition has a pH of between about 7.0 and about 10.2, and
  d. the eluting is done at a flow rate of between 0.2 CV/min and 5 CV/min.

[6.] A method for improving the separation between empty or partially filled recombinant adeno-associated virus (rAAV) particles and full rAAV particles during anion exchange chromatography comprising:
  (a) contacting a feed composition containing empty, partially filled and full rAAV particles with an anion exchange chromatography media under conditions that allow binding of the rAAV particles to the chromatography media;
  (b) eluting the rAAV particles from the chromatography media using a linear gradient; and
  (c) recovering an eluate comprising the eluted rAAV particles;
wherein the method is characterized by one or more of:
  a. the feed composition has a $Mg^{2+}$ concentration of between about 0.1 mM and about 20 mM,
  b. the feed composition has a $K^+$ concentration of between about 0.1 mM and about 20 mM,
  c. the feed composition has a pH of between about 6.5 and about 10.5,
  d. the eluting is done at a flow rate of between 0.1 CV/min and 5 CV/min, and
  e. the linear salt gradient comprises a volume of between about 5 and about 100 CV.

[7.] A method for improving the separation between recombinant adeno-associated virus (rAAV) particles and viral aggregates during anion exchange chromatography comprising:
  (a) contacting a feed composition containing rAAV particles and viral aggregates with an anion exchange chromatography media comprising under conditions that allow binding of the rAAV particles to the chromatography media;
  (b) eluting the rAAV particles from the chromatography media using a linear gradient; and
  (c) recovering an eluate comprising the eluted rAAV particles;
wherein the method is characterized by one or more of:
  a. the feed composition has a $Mg^{2+}$ concentration of between about 0.1 mM and about 20 mM,
  b. the feed composition has a $K^+$ concentration of between about 0.1 mM and about 20 mM,
  c. the feed composition has a pH of between about 6.5 and about 10.5,
  d. the eluting is done at a flow rate of between 0.1 CV/min and 5 CV/min, and
  e. the linear salt gradient comprises a volume of between about 5 and about 100 CV.

[8.] The method of [6] or [7], wherein the method is characterized by two or more of:
  a. the feed composition has a $Mg^{2+}$ concentration of between about 0.1 mM and about 20 mM,
  b. the feed composition has a $K^+$ concentration of between about 0.1 mM and about 20 mM,
  c. the feed composition has a pH of between about 6.5 and about 10.5,
  d. the eluting is done at a flow rate of between 0.1 CV/min and 5 CV/min, and
  e. the linear salt gradient comprises a volume of between about 5 and about 100 CV.

[9.] The method of [6] or [7], wherein the method is characterized by that
a. the feed composition has a Mg2+ concentration of between about 0.1 mM and about 20 mM,
b. the feed composition has a K+ concentration of between about 0.1 mM and about 20 mM,
c. the feed composition has a pH of between about 6.5 and about 10.5,
d. the eluting is done at a flow rate of between 0.2 CV/min and 5 CV/min, and
e. the linear salt gradient comprises a volume of between about 5 and about 100 CV.

[10.] The method of [6] or [7], wherein the method is characterized by that
a. the feed composition has a Mg2+ concentration of between about 0.1 mM and about 20 mM,
b. the feed composition has a K+ concentration of between about 0.1 mM and about 20 mM, and
c. the feed composition has a pH of between about 6.5 and about 10.5.

[11.] The method of [6] or [7], wherein the method is characterized by that
a. the feed composition has a Mg2+ concentration of between about 0.5 mM and about 10 mM,
b. the feed composition has a K+ concentration of between about 0.5 mM and about 10 mM, and
c. the feed composition has a pH of between about 6.5 and about 10.5.

[12.] The method of any one of [1] to [11], wherein the anion exchange chromatography media comprises a quaternary amine functional group.

[13.] The method of any one of [1] to [11], wherein the anion exchange chromatography media is a monolith anion exchange chromatography.

[14.] The method of any one of [1] to [11], wherein the anion exchange chromatography media is a monolith anion exchange chromatography comprising a quaternary amine functional group.

[15.] The method of any one of [1] to [14], wherein the linear salt gradient comprises between about 0 and 500 mM NaCl.

[16.] The method of any one of [1] to [14], wherein the linear salt gradient comprises between about 0 and 200 mM NaCl.

[17.] The method of any one of [1] to [16], further comprising washing the chromatography media comprising the bound rAAV particles prior to eluting.

[18.] The method of any one of [1] to [16], further comprising washing the chromatography media comprising the bound rAAV particles prior to eluting, wherein the wash buffer comprises between about 0.1 mM and about 20 mM Mg2+.

[19.] The method of any one of [1] to [16], further comprising washing the chromatography media comprising the bound rAAV particles prior to eluting, wherein the wash buffer comprises between about 0.1 mM and about 20 mM K+.

[20.] The method of any one of [1] to [16], further comprising washing the chromatography media comprising the bound rAAV particles prior to eluting, wherein the wash buffer comprises between about 0.1 mM and about 20 mM Mg2+ and between about 0.1 mM and about 20 mM K+.

[21.] The method of any one of [1] to [16], further comprising washing the chromatography media comprising the bound rAAV particles prior to eluting, wherein the wash buffer comprises 8 mM MgCl2 and 2.5 mM KCl.

[22.] The method of any one of [1] to [21], wherein the anion exchange chromatography media has been equilibrated with a buffer comprising 8 mM MgCl2 and 2.5 mM KCl prior to contacting the feed composition with the anion exchange chromatography media.

[23.] The method of any one of [1] to [22], wherein the rAAV particles comprise a capsid protein from an AAV selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

[24.] The method of any one of [1] to [22], wherein the rAAV particles comprise a capsid protein of the AAV-8 or AAV-9 serotype.

[25.] The method of any one of [1] to [24], wherein the feed composition has a pH of between about 8.2 and about 9.5.

[26.] The method of any one of [1] to [22], wherein the rAAV particles comprise a capsid protein of the AAV-8 serotype and the feed composition has a pH of between 8.2 and 8.6 or the rAAV particles comprise a capsid protein of the AAV-9 serotype and the feed composition has a pH of between 9.1 and 9.5.

[27.] The method of any one of [1] to [26], wherein the eluting is done at a flow rate of between 0.5 CV/min and 1.25 CV/min.

[28.] The method of any one of [1] to [27], wherein the linear salt gradient comprises 0 to 200 mM NaCl in a volume of between about 30 and about 70 CV.

[29.] The method of any one of [1] to [22], wherein the rAAV particles comprise a capsid protein of the AAV-8 or AAV-9 serotype, and wherein the method is characterized by two or more of:
a. the feed composition has a Mg2+ concentration of between about 0.5 mM and about 10 mM,
b. the feed composition has a K+ concentration of between about 0.5 mM and about 10 mM,
c. the rAAV particles comprise a capsid protein of the AAV-8 serotype and the feed composition has a pH of between 8.2 and 8.6 or the rAAV particles comprise a capsid protein of the AAV-9 serotype and the feed composition has a pH of between 9.1 and 9.5,
d. the eluting is done at a flow rate of between 1.25 CV/min and 0.5 CV/min, and
e. the linear salt gradient comprises a volume of between about 30 and about 70 CV.

[30.] The method of any one of [1] to [22], wherein the rAAV particles comprise a capsid protein of the AAV-8 or AAV-9 serotype, and wherein
a. the feed composition has a Mg2+ concentration of between about 0.5 mM and about 10 mM,
b. the feed composition has a K+ concentration of between about 0.5 mM and about 10 mM,
c. the rAAV particles comprise a capsid protein of the AAV-8 serotype and the feed composition has a pH of between 8.2 and 8.6 or the rAAV particles comprise a capsid protein of the AAV-9 serotype and the feed composition has a pH of between 9.1 and 9.5,
d. the eluting is done at a flow rate of between 1.25 CV/min and 0.5 CV/min, and
e. the linear salt gradient comprises a volume of between about 30 CV and about 70 CV.
[31.] The method of [29] or [30], wherein the salt gradient comprises 0 to 200 mM NaCl.
[32.] The method of any one of [1] to [31], wherein the feed composition has a Mg2+ concentration of 2.5 mM.
[33.] The method of any one of [1] to [31], wherein the feed composition has a Mg2+ concentration of 1 mM.
[34.] The method of any one of [1] to [33], wherein the feed composition has a K+ concentration of 1 mM.
[35.] The method of any one of [1] to [34], wherein the rAAV particles comprise a capsid protein of the AAV-8 serotype and the feed composition has a pH of about 8.4.
[36.] The method of any one of [1] to [34], wherein the rAAV particles comprise a capsid protein of the AAV-9 serotype and the feed composition has a pH of about 9.3.
[37.] The method of any one of [1] to [36], wherein the eluting is done at a flow rate of about 0.5 CV/min.
[38.] The method of any one of [1] to [37], wherein the linear salt gradient comprises 0 to 200 mM NaCl in a volume of about 50 CV.
[39.] The method of any one of [1] to [37], wherein the linear salt gradient comprises 0 to 200 mM NaCl in a volume of about 60 CV. [40.] The method of any one of [1] to [39], wherein the Mg2+ is MgCl2
[41.] The method of any one of [1] to [40], wherein the K+ is KCl.
[42.] The method of any one of [1] to [41], wherein the monolith anion exchange chromatography media comprises methacrylates, agrarose based materials, cellulose, acrylamides, polystyrene divinyl benzene or silica based materials.
[43.] The method of any one of [1] to [41], wherein the monolith anion exchange chromatography media comprises glycidylmethacrylate-ethylenedimethacrylate or styrene-divinylbenzene polymers.
[44.] The method of [43], wherein the monolith anion exchange chromatography media comprises glycidylmethacrylate-ethylenedimethacrylate polymers.
[45.] The method of any one of [1] to [44], wherein the monolith anion exchange chromatography media has an average pore radius of 950 nm to 1150 nm.
[46.] The method of any one of [1] to [44], wherein the monolith anion exchange chromatography media has an average pore radius of 600 nm to 750 nm.
[47.] The method of any one of [1] to [46], wherein the yield of rAAV particles is at least about 40%.
[48.] The method of any one of [1] to [46], wherein the yield of rAAV particles is at least about 50%.
[49.] The method of any one of [1] to [46], wherein the yield of rAAV particles is at least about 60%.
[50.] The method of any one of [1] to [46], wherein the yield of rAAV particles is at least about 70%.
[51.] The method of any one of [1] to [46], wherein the yield of rAAV particles is at least about 75%.
[52.] The method of any one of [1] to [46], wherein the yield of rAAV particles is at least about 80%.
[53.] The method of any one of [1] to [46], wherein the yield of rAAV particles is at least about 85%.
[54.] The method of any one of [1] to [46], wherein the yield of rAAV particles is at least about 90%.
[55.] The method of any one of [1] to [46], wherein the yield of rAAV particles is at least about 95%.
[56.] The method of any one of [1] to [55], wherein the impurity comprises an empty or partially filled viral capsid and the method separates the rAAV particles from the empty or partially filled viral capsid.
[57.] The method of any one of [1] to [56], wherein at least about 10%, at least about 20%, or at least about 30% of the viral capsids in the eluate are rAAV particles.
[58.] The method of any one of [1] to [56], wherein at least about 40% of the viral capsids in the eluate are rAAV particles.
[59.] The method of any one of [1] to [56], wherein at least about 50% of the viral capsids in the eluate are rAAV particles.
[60.] The method of any one of [1] to [56], wherein at least about 60% of the viral capsids in the eluate are rAAV particles.
[61.] The method of any one of [1] to [56], wherein at least about 70% of the viral capsids in the eluate are rAAV particles.
[62.] The method of any one of [1] to [56], wherein at least about 80% of the viral capsids in the eluate are rAAV particles.
[63.] The method of any one of [1] to [56], wherein at least about 90% of the viral capsids in the eluate are rAAV particles.
[64.] The method of any one of [1] to [56], wherein at least about 95% of the viral capsids in the eluate are rAAV particles.
[65.] The method of any one of [1] to [56], wherein at least about 97% of the viral capsids in the eluate are rAAV particles.
[66.] The method of any one of [1] to [56], wherein at least about 98% of the viral capsids in the eluate are rAAV particles.
[67.] The method of any one of [1] to [56], wherein at least about 99% of the viral capsids in the eluate are rAAV particles.
[68.] The method of any one of [1] to [67], wherein the feed composition is produced by
  (a) providing a starting composition comprising a cell culture, a cell lysate, cell supernatant, or combination thereof comprising the rAAV particles;
  (b) clarifying the starting composition by depth filtration to produce a clarified starting composition;
  (c) concentrating the clarified starting composition by tangential flow filtration to produce a concentrated filtrate;
  (d) contacting the concentrated filtrate with an affinity chromatography media; and
  (e) recovering the rAAV particles from the affinity chromatography media to produce the feed composition.
[69.] The method of any one of [1] to [67], wherein the feed composition is produced by
  (a) providing a starting composition comprising a cell culture, a cell lysate, cell supernatant, or combination thereof comprising the rAAV particles;
  (b) concentrating the clarified starting composition by tangential flow filtration to produce a concentrated filtrate;
  (c) contacting the concentrated filtrate with an affinity chromatography media; and (d) recovering the rAAV particles from the affinity chromatography media to produce the feed composition.

[70.] The method of [68] or [69], wherein the starting composition comprises a cell culture and the cell culture is a suspension culture or an adherent cell culture.

[71.] The method of [70], wherein the suspension culture comprises a culture of HeLa cells, HEK293 cells, HEK293 derived cells, Vero cells, CHO cells, EB66 cells, or SF-9 cells.

[72.] The method of [71], wherein the suspension culture comprises a culture of HEK293 cells.

[73.] The method of any one of [68] to [70], wherein the starting composition comprises a culture of mammalian cells or insect cells.

[74.] The method of any one of [68] to [70], wherein the starting composition comprises a culture of HeLa cells, HEK293 cells, HEK293 derived cells, Vero cells, CHO cells, EB66 cells, or SF-9 cells.

[75.] The method of any one of [68] to [74], wherein the starting composition has a volume of between about 20 liters and about 20,000 liters.

[76.] The method of any one of [68] to [74], wherein the starting composition has a volume of between about 20 liters and about 5,000 liters.

[77.] The method of any one of [68] to [74], wherein the starting composition has a volume of between about 50 liters and about 20,000 liters.

[78.] The method of any one of [68] to [74], wherein the starting composition has a volume of between about 50 liters and about 5,000 liters.

[79.] The method of any one of [68] to [74], wherein the starting composition has a volume of between about 100 liters and about 3,000 liters.

[80.] The method of any one of [68] to [74], wherein the starting composition has a volume of between about 500 liters and about 3,000 liters.

[81.] The method of any one of [68] to [74], wherein the starting composition has a volume of between about 1,500 liters and about 2,500 liters.

[82.] The method of [81], wherein the starting composition has a volume of about 2,000 liters.

[83.] The method of [81], wherein the starting composition has a volume of about 1000 liters.

[84.] A composition comprising isolated recombinant adeno-associated virus particles that were produced by the method of any one of [1] to [83].

In some embodiments, the methods include upstream processing to prepare the starting composition containing rAAV particles used according to the method of any one of [1] to [55]. In further embodiments, the upstream processing is at least one of harvest of a cell culture or cell culture supernatant, clarification of the harvested cell culture or cell culture supernatant (e.g., by centrifugation or depth filtration), tangential flow filtration, affinity chromatography, cation exchange chromatography, size exclusion chromatography, hydrophobic interaction chromatography, sterile filtration. In further embodiments, the upstream processing includes at least 2, at least 3, or at least 4 of: addition of harvest of a cell culture or cell culture supernatant, clarification of the harvested cell culture or cell culture supernatant (e.g., by centrifugation or depth filtration), tangential flow filtration, affinity chromatography, cation exchange chromatography, size exclusion chromatography, hydrophobic interaction chromatography, sterile filtration. In some embodiments, the upstream processing does not include centrifugation of the starting composition.

In additional embodiments, the methods include further downstream processing of the rAAV containing eluate from the anion exchange chromatography media recovered according to the method of any one of [1] to [55]. In some embodiments, the further downstream processing includes at least one of tangential flow filtration, cation exchange chromatography, hydrophobic interaction chromatography, size exclusion chromatography, or sterile filtration. In some embodiments, the further downstream processing includes at least 2, at least 3, or at least 4 of: tangential flow filtration, cation exchange chromatography, hydrophobic interaction chromatography, size exclusion chromatography, or sterile filtration. In some embodiments, the further downstream processing includes tangential flow filtration. In some embodiments, the further downstream processing includes sterile filtration. In further embodiments, the further downstream processing includes tangential flow filtration and sterile filtration.

BRIEF DESCRIPTION OF THE DRAWINGS

FIG. 4A-4C. Buffer system comprising $Mg^{2+}$ and $K^+$ provides good separation of AAV8-B full particles from product related impurities in various AEX chromatography resins comprising a quaternary amine. Chromatography runs using CIMmultus™ QA (BIA Separations) (A), Poros XQ (Thermo Fisher) (B), Sartobind® Q (Sartorius) (C) are shown.

FIG. 8A-8B. AAV9 purification using CIMmultus® QA column. Chromatography runs without added 2.5 mM $Mg^{2+}$ and 1 mM (A) and with 1 mM $Mg^{2+}$ and 1 mM (B) are shown.

DETAILED DESCRIPTION

Figure 1A:
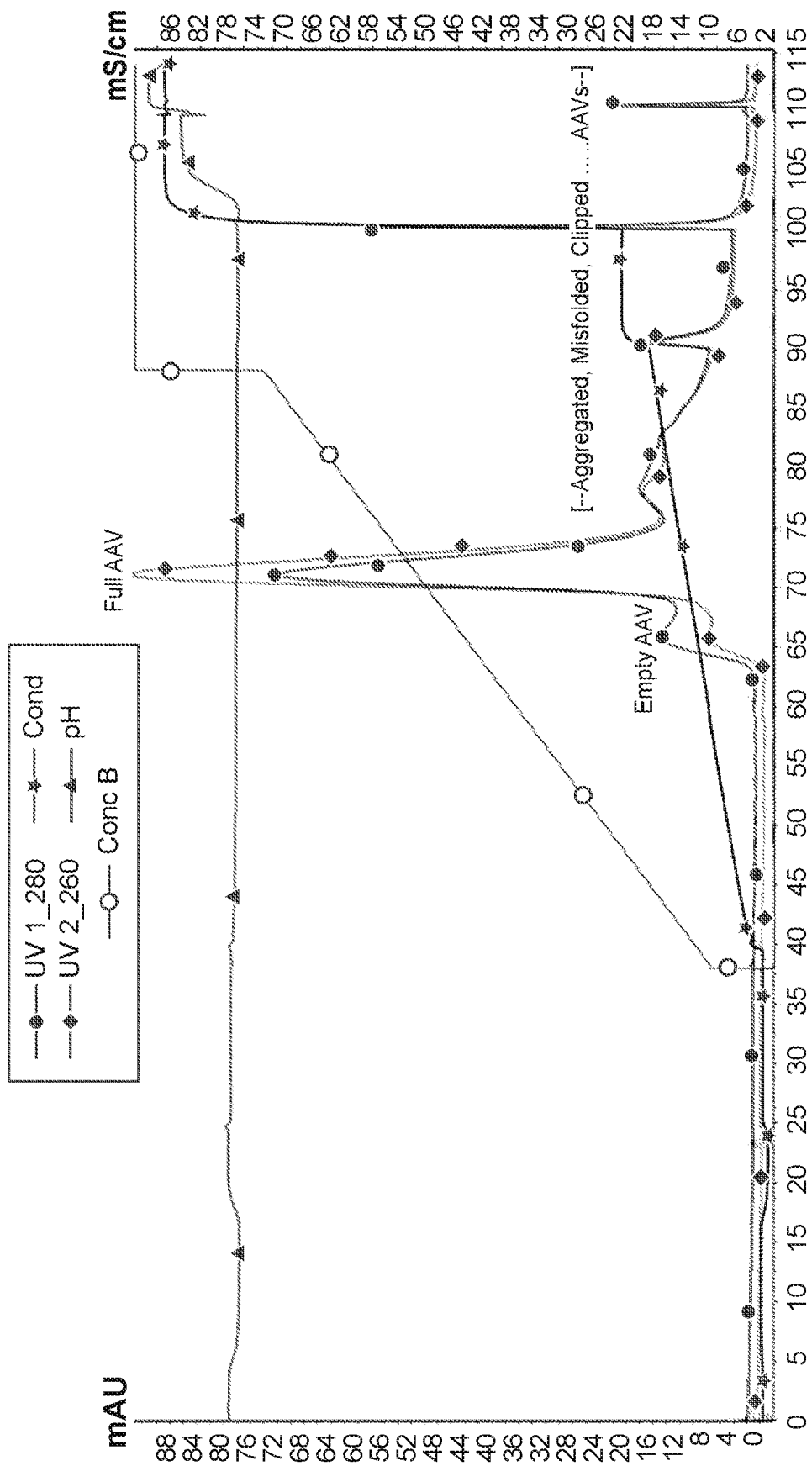
FIGS. 1A-1E. Screening of AEX resins for AAV8-A purification. The resins tested are (A) CIMmultus® QA, (B) Q Sepharose, (C) Fractogel® TMAE (M), (D) Toyopearl® Gigacap Q-650M, and (E) POROS™ 50 HQ.

In some embodiments, the disclosure provides methods for isolating rAAV particles from a feed composition comprising an impurity (e.g., an empty viral capsid or a viral aggregate) using AEX chromatography, methods for improving the separating of full rAAV viral particles from empty/partially filled particles during AEX chromatography, and methods for improving the separation of full rAAV viral particles from viral aggregates during AEX chromatography. In some embodiments, the method uses an anion exchange chromatography media comprising a quaternary amine ligand. In some embodiments, the method uses a anion exchange chromatography media. In some embodiments, the product of the method is suitable for further downstream processing, for example, by tangential flow filtration and sterile filtration, to produce isolated rAAV particles. The described methods provide flexible, cost-effective, commercially scalable processes consistent with GMP regulatory requirements for isolation of a population of rAAV particles for use in gene therapy applications. The methods described herein are suited to any rAAV serotype, including without limitation AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16, and derivatives, modifications, or pseudotypes thereof. In some embodiments, the methods are used to isolate rAAV-8 particles. In some embodiments, the methods are used to isolate rAAV-8 derivative particles, rAAV-8 modification particles, or rAAV-8 pseudotype particles. In some embodiments, the methods are used to isolate rAAV-9 particles. In some embodiments, the methods are used to isolate rAAV-9 derivative particles, rAAV-9 modification particles, or rAAV-9 pseudotype particles.

Methods disclosed herein provide several significant advantages. The increased virus yield of the methods disclosed herein provide significant cost savings for the industrial scale production of therapeutic AAV compositions. A 5% increase in virus yield allows a corresponding reduction not only in the cost of consumables needed to produce AAV particles, but also in the cost of capital expenditure in connection with building industrial virus purification facilities. The methods disclosed herein result in the production of safer therapeutic AAV preparations. The disclosed methods result in an improved separation of functional full rAAV particles from empty/partially filled capsids and virus aggregates. Because of the more efficient elimination of empty/partially filled capsids, therapeutic AAV formulations produced by the methods disclosed herein comprise less capsid proteins in a single unit dosage of functional AAV particles. Immune reaction against AAV capsid proteins is a potential side effect of AAV mediated gene therapy. By reducing the capsid proteins in a unit dosage of functional AAV particles, the methods disclosed herein make the therapeutic rAAV formulations safer by reducing the chance of an immune reaction against the capsid proteins.

Definitions

Unless defined otherwise, all technical and scientific terms used herein have the same meaning as commonly understood by one of ordinary skill in the art to which this disclosure is related. To facilitate an understanding of the disclosed methods, a number of terms and phrases are defined below.

"About" modifying, for example, the quantity of an ingredient in the compositions, concentration of an ingredient in the compositions, flow rate, rAAV particle yield, feed volume, salt concentration, and like values, and ranges thereof, employed in the methods provided herein, refers to variation in the numerical quantity that can occur, for example, through typical measuring and handling procedures used for making concentrates or use solutions; through inadvertent error in these procedures; through differences in the manufacture, source, or purity of the ingredients employed to make the compositions or carry out the methods; and like considerations. The term "about" also encompasses amounts that differ due to aging of a composition with a particular initial concentration or mixture. The term "about" also encompasses amounts that differ due to mixing or processing a composition with a particular initial concentration or mixture. Whether or not modified by the term "about" the claims include equivalents to the quantities. In some embodiments, the term "about" refers to ranges of approximately 10-20% greater than or less than the indicated number or range. In further embodiments, "about" refers to plus or minus 10% of the indicated number or range. For example, "about 10%" indicates a range of 9% to 11%.

"AAV" is an abbreviation for adeno-associated virus, and may be used to refer to the virus itself or modifications, derivatives, or pseudotypes thereof. The term covers all subtypes and both naturally occurring and recombinant forms, except where required otherwise. The abbreviation "rAAV" refers to recombinant adeno-associated virus. The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV, and modifications, derivatives, or pseudotypes thereof. "Primate AAV" refers to AAV that infect primates, "non-primate AAV" refers to AAV that infect non-primate mammals, "bovine AAV" refers to AAV that infect bovine mammals, etc.

"Recombinant", as applied to a an AAV particle means that the AAV particle is the product of one or more procedures that result in an AAV particle construct that is distinct from an AAV particle in nature.

A recombinant Adeno-associated virus particle "rAAV particle" refers to a viral particle composed of at least one AAV capsid protein and an encapsidated polynucleotide rAAV vector comprising a heterologous polynucleotide (i.e. a polynucleotide other than a wild-type AAV genome such as a transgene to be delivered to a mammalian cell). The rAAV particle may be of any AAV serotype, including any modification, derivative or pseudotype (e.g., AAV-1, AAV-2, AAV-3, AAV-4, AAV-5, AAV-6, AAV-7, AAV-8, AAV-9, or AAV-10, or derivatives/modifications/pseudotypes thereof). Such AAV serotypes and derivatives/modifications/pseudotypes, and methods of producing such serotypes/derivatives/modifications/pseudotypes are known in the art (see, e.g., Asokan et al., Mol. Ther. 20(4):699-708 (2012).

An "empty capsid" or "empty particle" refers to a virion that comprises at least one AAV capsid protein but lacks in whole or part the polynucleotide (artificial genome). Empty capsids do not include, e.g., an intact rAAV vector comprising a heterologous polynucleotide (such as a transgene to be delivered to a mammalian cell, i.e. a polynucleotide other than a wild-type AAV genome).

The rAAV particles of the disclosure may be of any serotype, or any combination of serotypes, (e.g., a population of rAAV particles that comprises two or more serotypes, e.g., comprising two or more of rAAV2, rAAV8, and rAAV9 particles). In some embodiments, the rAAV particles are rAAV1, rAAV2, rAAV3, rAAV4, rAAV5, rAAV6, rAAV7, rAAV8, rAAV9, rAAV10, or other rAAV particles, or combinations of two or more thereof). In some embodiments, the rAAV particles are rAAV8 or rAAV9 particles.

In some embodiments, the rAAV particles have an AAV capsid protein of a serotype selected from the group consisting of AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16 or a derivative, modification, or pseudotype thereof. In some embodiments, the rAAV particles have an AAV capsid protein of a serotype of AAV-8, AAV-9, or a derivative, modification, or pseudotype thereof.

The term "impurity" or "contaminant" refers to any foreign or objectionable molecule, including a biological macromolecule such as DNA, RNA, one or more host cell proteins, endotoxins, lipids and one or more additives which may be present in a sample containing the rAAV particles that are being separated from one or more of the foreign or objectionable molecules using a disclosed method. The term "impurity" or "contaminant" further encompasses product-related impurities, for example, inactive vector forms, empty viral capsids, aggregated viral particles or capsids, mis-folded viral capsids, degraded viral particles. In some embodiments, an impurity comprises an empty viral capsid or a viral aggregate. Additionally, such impurity may include any reagent which is used in a step which may occur prior to one or more of the disclosed methods. An impurity may be soluble or insoluble in nature. Insoluble impurities include any undesirable or objectionable entity present in a sample containing rAAV particles, where the entity is a suspended particle or a solid. Exemplary insoluble impurities include without limitation, aggregated viral particles or capsids, whole cells, cell fragments and cell debris. Soluble impurities include any undesirable or objectionable entity present in a sample containing rAAV particles where the entity is not an insoluble impurity. Exemplary soluble impurities include without limitation, host cell proteins, DNA, RNA, lipids viruses, endotoxins, and cell culture media components.

The term "cell culture," refers to cells grown adherent or in suspension, bioreactors, roller bottles, hyperstacks, microspheres, macrospheres, flasks and the like, as well as the components of the supernatant or suspension itself, including but not limited to rAAV particles, cells, cell debris, cellular contaminants, colloidal particles, biomolecules, host cell proteins, nucleic acids, and lipids, and flocculants. Large scale approaches, such as bioreactors, including suspension cultures and adherent cells growing attached to microcarriers or macrocarriers in stirred bioreactors, are also encompassed by the term "cell culture." Cell culture procedures for both large and small-scale production of proteins are encompassed by the present disclosure.

The terms "lysate" or "cell lysate" refer to a composition primarily consisting of cells that have ruptured cell walls and/or cell membranes. Lysates may or may not have been fractionated to remove one or more cellular components.

The terms "cell supernatant" or "cell culture supernatant" refer to the liquid media and extracellular components in the media suspension which may be separated from cellular material of an adherent cell culture or cell suspension culture. Generally, material secreted form the cells in culture may be purified from the cell supernatant. In some instances, AAV particles may be secreted into the supernatant and purified therefrom, with or without lysing cells. See, e.g. Clement, N. and Grieger, J. C. *Molecular Therapy Methods & Clinical Development* (2016) 3, 16002; doi:10.1038/mtm.2016.2, and US Published Application No. 2006/0040137, published on Feb. 11, 2016, both of which are herein incorporated by reference.

The term "clarified liquid culture medium" or "clarified starting composition" is used herein to refer to a liquid culture medium such as a cell culture supernatant obtained from a mammalian, bacterial, or yeast cell culture that is substantially free (such as at least 90%, 92%, 94%, 96%, 98%, or 99% free) of mammalian, bacterial, or yeast cells.

The term "feed composition" refers to a source of rAAV particles that is loaded onto, passed through, or applied to a filter or chromatographic matrix. Feeds encompassed by the disclosure include production culture harvests, and materials isolated from previous chromatographic steps encompassed by the disclosed methods whether the material was present as flow-through from the previous step, bound and eluted in the previous step, present in the void volume of the previous step or present in any fraction obtained during the purification of rAAV particles. Such feeds may include one or more impurities or contaminants. In some embodiments, the feed containing rAAV particles further comprises product-related impurities such as empty viral capsids, aggregated viral particles or capsids, mis-folded viral capsids, degraded viral particles, and/or damaged rAAV particles. In some embodiments, the feed containing rAAV particles further comprises host cell contaminants, helper virus contaminants, and/or cell culture contaminants. In some embodiments, the host cell contaminants comprise host cell DNA, plasmids, or host cell protein. In additional embodiments, the helper virus contaminants comprise adenovirus particles, adenovirus DNA, adenovirus proteins, baculovirus particles, baculovirus DNA, or baculovirus proteins. In some embodiments, the cell culture contaminants comprise media components, serum albumin, or other serum proteins. In additional embodiments, the cell culture contaminants comprise media components.

The term "filtrate" or "throughput" is a term of art and means a fluid that is emitted from a filter (e.g., a depth filter, a pre-filter, a virus filter, or a tangential-flow filter) that includes a detectable amount of a rAAV.

The terms "purifying", "purification", "separate", "separating", "separation", "isolate", "isolating", or "isolation", as used herein, refer to increasing the degree of purity of rAAV particles from a sample comprising the target product and one or more impurities. Typically, the degree of purity of the target product is increased by removing (completely or partially) at least one impurity from the sample. In some embodiments, the degree of purity of the rAAV in a sample is increased by removing (completely or partially) one or more impurities from the sample by using a method described herein.

The term "monolith chromatography column" or "monolith chromatography media" is a term of art and refers to chromatography columns that contain three dimensional macroporous structures, i.e., a monoliths, as the stationary phase. Monoliths are a continuous piece of highly porous material, such as a porous monolithic methacrylate-based polymer, that can be created by polymerization of a monomeric solution. Monoliths have been developed from polystyrene, polysaccharides, polymethacrylate and other synthetic polymers. Monoliths contain interconnected flow channels with defined diameter. Mass transfer of target molecules within these channels is governed by convective flow of the mobile phase. Ligand (e.g., quaternary ammonium, DEAE) addition to the monolith substrates can be accomplished through a variety of well-developed techniques to generate chromatography columns. Non-limiting monolith chromatography columns include CIMmultus™ Disposable pre-packed chromatographic monolithic columns, CIMac™ Analytical Columns, CIM® line monolithic columns, UNO® Monolith Columns, and Chromolith® Monolithic HPLC Columns. Non-limiting monolith chromatography resins include CIMmultus™ QA-1 Advanced Composite Column (Quaternary amine), CIMmultus™ DEAE-1 Advanced Composite Column (Diethylamino), CIM® QA Disk (Quaternary amine), CIM® DEAE, CIM® EDA Disk (Ethylene diamino), UNO® Monolith Anion Exchange Columns.

The term "average pore radius" or "average pore size" is a term of art that describes the pore size of a chromatography resin or the porous material in a monolithic or any other chromatography column. In some embodiments, for spherical pores, the average size is an "average pore diameter" or "average pore radius". In some embodiments, for non-spherical pores, the average size refers to the "average largest dimension". In some embodiments, the size distribution of pores can be determined by using nitrogen gas adsorption and desorption isotherms and applying the Kelvin equation in the manner of the Barrett, Joyner, and Halenda algorithm (E. P. Barrett, L. G. Joyner and P. H. Halenda, J. Amer. Chem. Soc. 73, 373, 1951), assuming a cylindrical pore model. In some embodiments, the size distribution of pores can be determined by analyzing Scanning Electron Microscopy (SEM) images of monolith sections using a commercial statistical analysis software package to study the distribution of the pore sizes, or by manually measuring the pore diameters using the scale in the SEM images. See, e.g., Jungreuthmayer, Journal of Chromatography A, 1425: 141-149 (2015). In some embodiments, the "average pore size" or "average pore radius" can be determined by calculating the average diameter of 20 measured pores.

The term "depth filter" is a term of art and means a filter that includes a porous filtration media that captures contaminants and/or impurities within its 3-dimensional structure and not merely on the surface. Depth filter clarification media are typically constructed from materials of a fibrous bed of cellulose, a wet-strength resin binder and an inorganic filter aid such as diatomaceous earth. The resin binder helps to impart wet tensile strength, provide an adsorptive charge to bind impurities and minimize shedding of the filter components. The diatomaceous earth provides a high surface area to the filter and contributes to the adsorptive properties. Depth filter media, unlike absolute filters, retain particles throughout the filter media. Depth filters are characterized in that they retain the contaminants or impurities within the filter and can retain a relatively large quantity before becoming clogged. Depth filter construction may include multiple layers, multiple membranes, a single layer, or a resin material. Non-limiting examples of depth filters include CUNO® Zeta PLUS® Delipid filters, CUNO® Emphaze AEX filters, CUNO® 30/60ZA filters, CUNO® 90ZBO8A filters, CUNO® DELI08A Delipid filters, and CUNO® DELIP08A Delipid plus filters (3M, St. Paul, Minn.), Clarisolve® grade 60HX, 40MS, 20MS, Millistak+® HC grade COHC, DOHC, A1HC, B1HC, XOHC, FOHC, Millistak+® HC Pro grade DOSP, COSP, and XOSP Millipore filters (EMD Millipore, Billerica, Mass.), and Sartopore® bi-layer filter cartridges.

"Tangential flow filtration", "TFF" (also called cross-flow microfiltration), and the like are terms of art, that refer to a mode of filtration in which the solute-containing solution passes tangentially across the ultrafiltration membrane and lower molecular weight salts or solutes are passed through by applying pressure.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Where embodiments of the disclosure are described in terms of a Markush group or other grouping of alternatives, the disclosed method encompasses not only the entire group listed as a whole, but also each member of the group individually and all possible subgroups of the main group, and also the main group absent one or more of the group members. The disclosed methods also envisage the explicit exclusion of one or more of any of the group members in the disclosed methods.

Methods for rAAV Purification by Anion Exchange Chromatography

In some embodiments, the disclosure provides methods for isolating rAAV particles from a feed composition comprising an impurity, wherein the method comprises contacting the feed composition with an anion exchange chromatography media under conditions that allow binding of the rAAV particles to the chromatography media; and eluting the rAAV particles from the chromatography media; and recovering an eluate comprising the isolated rAAV particles, wherein the impurity comprises an empty or partially filled viral capsid or a viral aggregate. In some embodiments, the rAAV particles comprise a capsid protein of the AAV-8 or AAV-9 serotype, or a derivative or modification thereof. In some embodiments, the anion exchange chromatography media is a monolith chromatography media. In some embodiments, the anion exchange chromatography media comprises a quaternary amine functional group. In some embodiments, the monolith anion exchange chromatography media comprises a quaternary amine. In some embodiments, the feed composition comprises between about 0.1 mM and about 20 mM $Mg^{2+}$, $Ca^{2+}$, or $Zn^{2+}$. In some embodiments, the feed composition comprises between about 0.5 mM and about 10 mM $Mg^{2+}$, $Ca^{2+}$, or $Zn^{2+}$. In some embodiments, the feed composition comprises between about 0.1 mM and about 20 mM $Mg^{2+}$. In some embodiments, the feed composition comprises between about 0.5 mM and about 10 mM $Mg^{2+}$. In some embodiments, the feed composition comprises between about 1 mM and about 2.5 mM $Mg^{2+}$. In some embodiments, the feed composition comprises between about 0.1 mM and about 20 mM $K^+$, $Rb^+$, or $Cs^+$. In some embodiments, the feed composition comprises between about 0.5 mM and about 10 mM $K^+$, $Rb^+$, or $Cs^+$. In some embodiments, the feed composition comprises between about 0.1 mM and about 20 mM $K^+$. In some embodiments, the feed composition comprises between about 0.5 mM and about 10 mM $K^+$. In some embodiments, the feed composition comprises 1 mM $K^+$. In some embodiments, the feed composition has a pH of between about 7.0 and about 10.2, between about 8.2 and about 8.6, or between about 9.1 and about 9.5. In some embodiments, the rAAV particles comprise a capsid protein of the AAV-8 serotype, or a derivative or modification thereof, and the feed composition has a pH of between about 8.2 and about 8.6. In some embodiments, the rAAV particles comprise a capsid protein of the AAV-9 serotype, or a derivative or modification thereof, and the feed composition has a pH of between about 9.1 and about 9.5. In some embodiments, the eluting is done at a flow rate of between about 0.2 CV/min and about 5 CV/min. In some embodiments, the eluting is done at a flow rate of between about 0.5 CV/min and about 1.25 CV/min. In some embodiments, the eluting is done by a linear salt gradient. In some embodiments, the linear salt gradient comprises 0 to 500 mM NaCl in a volume of between about 30 and about 70 CV.

In some embodiments, the disclosure provides methods for improving the separation between recombinant adeno-associated virus (rAAV) particles and viral aggregates during anion exchange chromatography, wherein the method comprises contacting a feed composition containing rAAV particles and viral aggregates with an anion exchange chromatography media comprising under conditions that allow binding of the rAAV particles to the chromatography media; eluting the rAAV particles from the chromatography media; and recovering an eluate comprising the isolated rAAV particles. In some embodiments, the rAAV particles comprise a capsid protein of the AAV-8 or AAV-9 serotype, or a derivative or modification thereof. In some embodiments, the anion exchange chromatography media is a monolith chromatography media. In some embodiments, the anion exchange chromatography media comprises a quaternary amine functional group. In some embodiments, the monolith anion exchange chromatography media comprises a quaternary amine. In some embodiments, the feed composition comprises between about 0.1 mM and about 20 mM $Mg^{2+}$, $Ca^{2+}$, or $Zn^{2+}$. In some embodiments, the feed composition comprises between about 0.5 mM and about 10 mM $Mg^{2+}$, $Ca^{2+}$, or $Zn^{2+}$. In some embodiments, the feed composition comprises between about 0.1 mM and about 20 mM $Mg^{2+}$. In some embodiments, the feed composition comprises between about 0.5 mM and about 10 mM $Mg^{2+}$. In some embodiments, the feed composition comprises between about 1 mM and about 2.5 mM $Mg^{2+}$. In some embodiments, the feed composition comprises between about 0.1 mM and about 20 mM $Rb^+$, or $Cs^+$. In some embodiments, the feed composition comprises between about 0.5 mM and about 10 mM $K^+$, $Rb^+$, or $Cs^+$. In some embodiments, the feed composition comprises between about 0.1 mM and about 20 mM $K^+$. In some embodiments, the feed composition comprises between about 0.5 mM and about 10 mM $K^+$. In some embodiments, the feed composition comprises 1 mM $K^+$. In some embodiments, the feed composition has a pH of between about 7.0 and about 10.2, between about 8.2 and about 8.6, or between about 9.1 and about 9.5. In some embodiments, the rAAV particles comprise a capsid protein of the AAV-8 serotype, or a derivative or modification thereof, and the feed composition has a pH of between about 8.2 and about 8.6. In some embodiments, the rAAV particles comprise a capsid protein of the AAV-9 serotype, or a derivative or modification thereof, and the feed composition has a pH of between about 9.1 and about 9.5. In some embodiments, the eluting is done at a flow rate of between about 0.2 CV/min and about 5 CV/min. In some embodiments, the eluting is done at a flow rate of between about 0.5 CV/min and about 1.25 CV/min. In some embodiments, the eluting is done by a linear salt gradient. In some embodiments, the linear salt gradient comprises 0 to 500 mM NaCl in a volume of between about 5 and about 100 CV.

In some embodiments, the disclosure provides methods for improving the separation between recombinant adeno-associated virus (rAAV) particles and viral aggregates during anion exchange chromatography, wherein the method comprises contacting a feed composition containing rAAV particles and viral aggregates with an anion exchange chromatography media comprising under conditions that allow binding of the rAAV particles to the chromatography media; eluting the rAAV particles from the chromatography media; and recovering an eluate comprising the isolated rAAV particles. In some embodiments, the rAAV particles comprise a capsid protein of the AAV-8 or AAV-9 serotype, or a derivative or modification thereof. In some embodiments, the anion exchange chromatography media is a monolith chromatography media. In some embodiments, the anion exchange chromatography media comprises a quaternary amine functional group. In some embodiments, the monolith anion exchange chromatography media comprises a quaternary amine. In some embodiments, the feed composition comprises between about 0.1 mM and about 20 mM $Mg^{2+}$, $Ca^{2+}$, or $Zn^{2+}$. In some embodiments, the feed composition comprises between about 0.5 mM and about 10 mM $Mg^{2+}$, $Ca^{2+}$, or $Zn^{2+}$. In some embodiments, the feed composition comprises between about 0.1 mM and about 20 mM $Mg^{2+}$. In some embodiments, the feed composition comprises between about 0.5 mM and about 10 mM $Mg^{2+}$.In some embodiments, the feed composition comprises between about 1 mM and about 2.5 mM $Mg^{2+}$. In some embodiments, the feed composition comprises between about 0.1 mM and about 20 mM $K^+$, $Rb^+$, or $Cs^+$. In some embodiments, the feed composition comprises between about 0.5 mM and about 10 mM $K^+$, $Rb^+$, or $Cs^+$. In some embodiments, the feed composition comprises between about 0.1 mM and about 20 mM $K^+$. In some embodiments, the feed composition comprises between about 0.5 mM and about 10 mM $K^+$. In some embodiments, the feed composition comprises 1 mM $K^+$. In some embodiments, the feed composition has a pH of between about 7.0 and about 10.2, between about 8.2 and about 8.6, or between about 9.1 and about 9.5. In some embodiments, the rAAV particles comprise a capsid protein of the AAV-8 serotype, or a derivative or modification thereof, and the feed composition has a pH of between about 8.2 and about 8.6. In some embodiments, the rAAV particles comprise a capsid protein of the AAV-9 serotype, or a derivative or modification thereof, and the feed composition has a pH of between about 9.1 and about 9.5. In some embodiments, the eluting is done at a flow rate of between about 0.2 CV/min and about 5 CV/min. In some embodiments, the eluting is done at a flow rate of between about 0.5 CV/min and about 1.25 CV/min. In some embodiments, the eluting is done by a linear salt gradient. In some embodiments, the linear salt gradient comprises 0 to 500 mM NaCl in a volume of between about 5 and about 100 CV.

In some embodiments, the anion exchange chromatography media is a strong anion exchange media. In some embodiments, the anion exchange chromatography media is a weak anion exchange media.

In some embodiments, the anion exchange chromatography media comprises a quaternary ammonium ligand. In some embodiments, the anion exchange chromatography media comprises a quaternary polyethyleneimine. In some embodiments, the monolith anion exchange chromatography media comprises diethylaminoethanol (DEAE) ligand. Examples of chromatography media comprising a quaternary ammonium ligand include, but are not limited to CIMmultus™ QA (BIA Separations), Poros XQ and HQ (Thermo Fisher), Sartobind® Q (Sartorius), Q Sepharose® (GE Healthcare), and Toyopearl® GigaCap Q-650M (Tosho Bioscience).

In some embodiments, the monolith anion exchange chromatography media comprises diethylaminoethanol (DEAE) ligand.

In some embodiments, the anion exchange chromatography media comprises methacrylates, agrarose based materials, cellulose, acrylamides, polystyrene divinyl benzene or silica based materials.

In some embodiments, the monolith anion exchange chromatography media comprises methacrylates, agrarose based materials, cellulose, acrylamides, polystyrene divinyl benzene or silica based materials. In some embodiments, the monolith anion exchange chromatography media comprises methacrylates or polystyrene divinyl benzene. In some embodiments, the monolith anion exchange chromatography media comprises methacrylates.

In some embodiments, the monolith anion exchange chromatography media comprises glycidylmethacrylate-ethylenedimethacrylate or styrene-divinylbenzene polymers. In some embodiments, the monolith anion exchange chromatography media comprises glycidylmethacrylate-ethylenedimethacrylate polymers.

In some embodiments, the monolith anion exchange chromatography media has an average pore radius of between about 400 nm and about 1500 nm. In some embodiments, the monolith anion exchange chromatography media has an average pore radius of between about 400 nm and about 900 nm. In some embodiments, the monolith anion exchange chromatography media has an average pore radius of about 600 nm to about 750 nm. In some embodiments, the monolith anion exchange chromatography media has an average pore radius of between about 800 nm and about 1300 nm. In some embodiments, the monolith anion exchange chromatography media has an average pore radius of about 950 nm to about 1150 nm.

In some embodiments, the monolith anion exchange chromatography media has an average pore diameter of between about 0.8 µm and about 3 µm. In some embodiments, the monolith anion exchange chromatography media has an average pore diameter of between about 0.8 µm and about 2 µm. In some embodiments, the monolith anion exchange chromatography media has an average pore diameter of about 2 µm to about 1.5 µm. In some embodiments, the monolith anion exchange chromatography media has an average pore diameter of between about 1.5 µm and about 2.5 µm. In some embodiments, the monolith anion exchange chromatography media has an average pore diameter of about 1.9 µm to about 2.4 µm. In some embodiments, the monolith anion exchange chromatography media has an average pore diameter of about 0.8 µm. In some embodiments, the monolith anion exchange chromatography media has an average pore diameter of about 1 µm. In some embodiments, the monolith anion exchange chromatography media has an average pore diameter of about 1.5 µm. In some embodiments, the monolith anion exchange chromatography media has an average pore diameter of about 2 µm. In some embodiments, the monolith anion exchange chromatography media has an average pore diameter of about 2.5 µm.

In some embodiments, the monolith anion exchange chromatography media comprises a quaternary ammonium ligand. In some embodiments, the monolith anion exchange chromatography media comprises diethylaminoethanol (DEAE) ligand.

In some embodiments, the monolith anion exchange chromatography media comprises methacrylate, a quaternary ammonium ligand, and has an average pore radius of about 950 nm to about 1150 nm. In some embodiments, the monolith anion exchange chromatography media comprises glycidylmethacrylate-ethylenedimethacrylate polymers, a quaternary ammonium ligand, and has an average pore radius of about 950 nm to about 1150 nm. In some embodiments, the monolith anion exchange chromatography media comprises methacrylate, a quaternary ammonium ligand, and has an average pore radius of about 600 nm to 750 nm. In some embodiments, the monolith anion exchange chromatography media comprises glycidylmethacrylate-ethylenedimethacrylate polymers, a quaternary ammonium ligand, and has an average pore radius of about 600 nm to 750 nm. In some embodiments, the monolith anion exchange chromatography media comprises methacrylate, a quaternary ammonium ligand, and has an average pore diameter of about 1.5 µm. In some embodiments, the monolith anion exchange chromatography media comprises glycidylmethacrylate-ethylenedimethacrylate polymers, a quaternary ammonium ligand, and has an average pore diameter of about 2 µm.

In some embodiments, the monolith anion exchange chromatography media is selected from the group consisting of CIMmultus™ QA-1 Advanced Composite Column (Quaternary amine), CIMmultus™ DEAE-1 Advanced Composite Column (Diethylamino), CIM® QA Disk (Quaternary amine), CIM® DEAE, and CIM® EDA Disk (Ethylene diamino). In some embodiments, the monolith anion exchange chromatography media is CIMmultus™ QA-1 Advanced Composite Column (Quaternary amine). In some embodiments, the monolith anion exchange chromatography media is CIM® QA Disk (Quaternary amine).

In some embodiments, the rAAV particles comprise a capsid protein from an AAV capsid serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise a capsid protein that is a derivative, modification, or pseudotype of AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 capsid protein.

In some embodiments, the rAAV particles comprise a capsid protein from an AAV capsid serotype selected from AAV-8 and AAV-9. In some embodiments, the rAAV particles have an AAV capsid serotype of AAV-8. In some embodiments, the rAAV particles have an AAV capsid serotype of AAV-9.

In some embodiments, the rAAV particles comprise a capsid protein that is a derivative, modification, or pseudotype of AAV-8 or AAV-9 capsid protein. In some embodiments, the rAAV particles comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-8 capsid protein.

In some embodiments, the rAAV particles composition comprise a capsid protein that is a derivative, modification, or pseudotype of AAV-9 capsid protein. In some embodiments, rAAV particles in the feed composition comprise a capsid protein that has an AAV-9 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-9 capsid protein.

In additional embodiments, the rAAV particles comprise a mosaic capsid. In additional embodiments, the rAAV particles comprise a pseudotyped rAAV particle. In additional embodiments, the rAAV particles comprise a capsid containing a capsid protein chimera of two or more AAV capsid serotypes.

In some embodiments, the feed composition comprises a monovalent cation. Various monovalent cations exist and are known to those skilled in the art, and include, e.g., lithium ($Li^+$), sodium ($Na^+$), potassium ($K^+$), rubidium ($Rb^+$), cesium ($Cs^+$), and francium ($Fr^+$), and combinations thereof. One of skill in the art will realize that the cation can exist in salt form, e.g., a potassium salt such as KCl can produce a potassium cation when placed in an aqueous solution. Thus, as used herein, the phrase "adding a monovalent cation" would encompass not only the addition of a cation in its charged stated, but also the addition of a salt or other compound that would produce a monovalent cation upon introduction into the feed composition of the present invention. In some embodiments, the monovalent cation is potassium ($K^+$).

In some embodiments, the feed composition comprises between about 0.1 mM and about 50 mM of a monovalent cation. In some embodiments, the feed composition comprises between about 0.1 mM and about 20 mM of a monovalent cation. In some embodiments, the feed composition comprises between about 0.2 mM and about 50 mM of a monovalent cation. In some embodiments, the feed composition comprises between about 0.2 mM and about 50 mM K. In some embodiments, the feed composition comprises between about 0.5 mM and about 10 mM $K^+$. In some embodiments, the feed composition comprises between about 0.1 mM and about 20 mM $K^+$. In some embodiments, the feed composition comprises between about 0.5 mM and about 10 mM $Rb^+$. In some embodiments, the feed composition comprises between about 0.1 mM and about 20 mM $Rb^+$. In some embodiments, the feed composition comprises between about 0.5 mM and about 10 mM $Cs^+$. In some embodiments, the feed composition comprises between about 0.1 mM and about 20 mM $Cs^+$. In some embodiments, the feed composition comprises about 1 mM $K^+$. In some embodiments, the $K^+$ is potassium chloride or potassium acetate. In some embodiments, the $K^+$ is potassium chloride.

In some embodiments, the feed composition comprises a divalent cation. Various divalent cations exist and are known to those in the art, and include, e.g., calcium cation ($Ca^{2+}$), magnesium cation ($Mg^{2+}$), copper cation ($Cu^{2+}$), cobalt cation ($Co^{2+}$), manganese cation ($Mn^{2+}$), nickel cation ($Ni^{2+}$), zinc cation ($Zn^{2+}$), and combinations thereof. One of skill in the art will realize that the cation can exist in salt form, e.g., a magnesium salt such as $MgCl_2$ can produce a magnesium cation when placed in an aqueous solution. Thus, as used herein, the phrase "adding a divalent cation" would encompass not only the addition of a cation in its charged stated, but also the addition of a salt or other compound that would produce a divalent cation upon introduction into the composition of the present invention. In some embodiments, the divalent cation is $Mg^{2+}$, $Mn^{2+}$, $Cu^{2+}$, $Zn^{2+}$, or their salts (e.g., $MgCl_2$, $MnCl_2$, $CuCl_2$, and $ZnCl_2$), or combinations of one or more of these cations or salts. In some embodiments, the divalent cation is $Mg^{2+}$, $Ca^{2+}$, $Zn^{2+}$, or their salts (e.g., $MgCl_2$, $CaCl_2$, and $ZnCl_2$), or combinations of one or more of these cations or salts.

In some embodiments, the feed composition comprises between about 0.1 mM and about 50 mM of a divalent cation. In some embodiments, the feed composition comprises between about 0.1 mM and about 20 mM of a divalent cation. In some embodiments, the feed composition comprises between about 0.2 mM and about 50 mM of a divalent cation. In some embodiments, the feed composition comprises between about 0.2 mM and about 50 mM $Mg^{2+}$. In some embodiments, the feed composition comprises between about 0.1 mM and about 20 mM $Mg^{2+}$. In some embodiments, the feed composition comprises between about 0.5 mM and about 10 mM $Mg^{2+}$. In some embodiments, the feed composition comprises between about 0.5 mM and about 5 mM $Mg^{2+}$. In some embodiments, the feed composition comprises about 1 mM $Mg^{2+}$. In some embodiments, the feed composition comprises about 1 mM $Mg^{2+}$. In some embodiments, the $Mg^{2+}$ is magnesium chloride. In some embodiments, the feed composition comprises between about 0.1 mM and about 20 mM Ca'. In some embodiments, the feed composition comprises between about 0.1 mM and about 20 mM In some embodiments, the feed composition comprises between about 0.1 mM and about 50 mM of a monovalent cation and between about 0.1 mM and about 50 mM of a divalent cation. In some embodiments, the feed composition comprises between about 0.1 mM and about 20 mM of a monovalent cation and between about 0.1 mM and about 20 mM of a divalent cation. In some embodiments, the feed composition comprises between about 0.2 mM and about 50 mM of a monovalent cation and between about 0.2 mM and about 50 mM of a divalent cation. In some embodiments, the feed composition comprises between about 0.1 mM and about 20 mM of $K^+$ and between about 0.1 mM and about 20 mM of a divalent $Mg^{2+}$. In some embodiments, the feed composition comprises between about 0.2 mM and about 50 mM $K^+$ and between about 0.2 mM and about 50 mM $Mg^{2+}$. In some embodiments, the feed composition comprises between about 0.5 mM and about 10 mM $K^+$ and between about 0.5 mM and about 10 mM $Mg^{2+}$. In some embodiments, the feed composition comprises between about 0.5 mM and about 5 mM $K^+$ and between about 0.5 mM and about 5 mM $Mg^{2+}$. In some embodiments, the feed composition comprises about 1 mM $K^+$ and about 1 mM $Mg^{2+}$. In some embodiments, the feed composition comprises about 1 mM and about 2.5 mM $Mg^{2+}$.

In some embodiments, the rAAV particles comprise an AAV capsid serotype of AAV-8, and the feed composition comprises about 1 mM $K^+$ and about 2.5 mM $Mg^{2+}$. In some embodiments, the rAAV particles comprise an AAV capsid serotype of AAV-9, and the feed composition comprises about 1 mM $K^+$ and about 1 mM $Mg^{2+}$.

In some embodiments, the feed composition comprises a buffering agent. In some embodiments, the Equilibration Buffer, Wash Buffer, and Elution Buffer comprises a buffering agent. In some embodiments, the buffering agent is Tris (e.g., Tris HCl), Bis-Tris Propane, Hepes, or phosphate buffer. In some embodiments, the buffering agent is Tris (e.g., Tris HCl).

In some embodiments, the feed composition further comprises between about 0.01% and about 0.5% nonionic surfactant. In some embodiments, the Equilibration Buffer, Wash Buffer, and Elution Buffer comprises between about 0.01% and about 0.5% nonionic surfactant. Pharmaceutically acceptable non-ionic surfactants include, without limitations, poloxamer 188, poloxamer 407, polysorbate 80, polysorbate 20, Pluronic F-68, or BRIJ 35. In some embodiments, a formulation disclosed herein comprises poloxamer 188, poloxamer 407, polysorbate 80, polysorbate 20, Pluronic F-68, BRIJ 35, or a combination thereof. In some embodiments, the feed composition comprises Pluronic F-68.

In some embodiments, the feed composition has a pH of between about 6.5 and about 10.5. In some embodiments, the feed composition has a pH of between about 7.0 and about 10.2. In some embodiments, the feed composition has a pH of between about 8.2 and about 9.5. In some embodiments, the feed composition has a pH of between about 8.2 and about 8.6. In some embodiments, the feed composition has a pH of between about 9.1 and about 9.5. In some embodiments, the feed composition has a pH of about 8.4. In some embodiments, the feed composition has a pH of about 9.3.

In some embodiments, the rAAV particles comprise an AAV capsid serotype of AAV-8, and the feed composition has a pH of between about 8.2 and about 8.6. In some embodiments, the rAAV particles comprise an AAV capsid serotype of AAV-9, and the feed composition has a pH of between about 9.1 and about 9.5.

In some embodiments, the rAAV particles comprise an AAV capsid serotype of AAV-8, and the feed composition has a pH of about 8.4. In some embodiments, the rAAV particles comprise an AAV capsid serotype of AAV-9, and the feed composition has a pH of about 9.3.

In some embodiments, the rAAV particles comprise an AAV capsid serotype of AAV-8, and the feed composition comprises about 1 mM $K^+$ and about 2.5 mM $Mg^{2+}$, and has a pH of about 8.4. In some embodiments, the rAAV particles comprise an AAV capsid serotype of AAV-9, and the feed composition comprises about 1 mM $K^+$ and about 1 mM $Mg^{2+}$, and has a pH of about 9.3.

One of skill in the art understands that anion exchange chromatography can encompass the use of a buffer system comprising multiple buffer compositions, such as an Equilibration Buffer to equilibrate the chromatography resin prior to loading the feed composition, a Wash Buffer to wash unbound impurities from the chromatography media after loading the feed composition, and Elution Buffer to elute bound materials, including the bound rAAV particles, from the chromatography media. In some embodiments, a method disclosed herein uses a buffer system comprising one or more of an Equilibration Buffer, Wash Buffer, and Elution Buffer. In some embodiments, a method disclosed herein uses a buffer system comprising two or more of an Equilibration Buffer, Wash Buffer, and Elution Buffer. In some embodiments, a method disclosed herein uses an Equilibration Buffer, Wash Buffer, and Elution Buffer.

In some embodiments, each member of the buffer system comprises between about 0.2 mM and about 50 mM of a monovalent cation and between about 0.2 mM and about 50 mM of a divalent cation, and has a pH of between 8.2 and 8.6 or between 9.1 and 9.5. In some embodiments, each member of the buffer system comprises between about 0.2 mM and about 50 mM of $K^+$ and between about 0.2 mM and about 50 mM of $Mg^{2+}$, and has a pH of between 8.2 and 8.6 or between 9.1 and 9.5. In some embodiments, each member of the buffer system comprises between about 0.5 mM and about 10 mM of $K^+$ and between about 0.5 mM and about 10 mM of $Mg^{2+}$, and has a pH of between 8.2 and 8.6 or between 9.1 and 9.5. In some embodiments, each member of the buffer system comprises between about 0.5 mM and about 5 mM of $K^+$ and between about 0.5 mM and about 5 mM of $Mg^{2+}$, and has a pH of between 8.2 and 8.6 or between 9.1 and 9.5. In some embodiments, each member of the buffer system comprises about 1 mM of $K^+$ and about 2.5 mM of $Mg^{2+}$, and has a pH of between 8.2 and 8.6 or between 9.1 and 9.5. In some embodiments, each member of the buffer system comprises about 1 mM of $K^+$ and about 1 mM of $Mg^{2+}$, and has a pH of between 8.2 and 8.6 or between 9.1 and 9.5. In some embodiments, each member of the buffer system comprises about 1 mM of $K^+$ and about 2.5 mM of $Mg^{2+}$, and has a pH of about 8.4. In some embodiments, each member of the buffer system comprises about 1 mM of $K^+$ and about 1 mM of $Mg^{2+}$, and has a pH of about 9.3.

In some embodiments, the rAAV particles comprise an AAV capsid serotype of AAV-8, each member of the buffer system comprises about 1 mM of $K^+$ and about 2.5 mM of $Mg^{2+}$, and each member of the buffer system has a pH of about 8.4. In some embodiments, the rAAV particles comprise an AAV capsid serotype of AAV-9, each member of the buffer system comprises about 1 mM of $K^+$ and about 1 mM of $Mg^{2+}$, and each member of the buffer system has a pH of about 9.3.

In some embodiments, the disclosed methods comprise equilibrating the anion exchange chromatography media with an Equilibration Buffer. In some embodiments, the anion exchange chromatography media is equilibrated prior to loading using a buffer comprising about the same divalent cation concentration, monovalent cation concentration, and pH as the feed composition. In some embodiments, the anion exchange chromatography media is equilibrated prior to loading using a buffer comprising about the same $Mg^{2+}$ concentration, $K^+$ concentration, and pH as the feed composition. In some embodiments, the anion exchange chromatography media is a chromatography column. Chromatography column can be equilibrated using any method known in the art. For example, the anion exchange chromatography column can be equilibrated by washing the column with 10 column-volume (CV) of Equilibration Buffer.

Contacting the feed composition with an anion exchange chromatography media encompasses loading the feed composition onto the anion exchange chromatography media (e.g., a monolith anion exchange chromatography column) using any methods known in the art.

In some embodiments, the disclosed methods comprise washing the anion exchange chromatography media (e.g., a monolith column) comprising the bound rAAV particles with a Wash Buffer to remove any unbound impurities. In some embodiment, the Wash Buffer comprises between about 0.1 mM and about 20 mM divalent cation and between about 0.1 mM and about 20 mM monovalent cation. In some embodiment, the Wash Buffer comprises about the same divalent cation concentration, monovalent cation concentration, and pH as the feed composition. In some embodiment, the Wash Buffer comprises between about 0.1 mM and about 20 mM $Mg^{2+}$. In some embodiment, the Wash Buffer comprises between about 0.1 mM and about 20 mM $K^+$. In some embodiment, the Wash Buffer comprises between about 0.1 mM and about 20 mM $Mg^{2+}$ and between about 0.1 mM and about 20 mM K⁺. In some embodiment, the Wash Buffer comprises 8 mM Mg²⁺ (e.g., MgCl₂) and 2.5 mM K+(e.g., KCl). In some embodiment, the wash buffer comprises about the same Mg²⁺ concentration, K⁺ concentration, and pH as the feed composition. In some embodiments, the anion exchange chromatography media is washed with between about 5 CV and 30 CV of Wash Buffer.

In some embodiments, rAAV particles bound to the anion exchange chromatography media (e.g., monolith column) are eluted with a gradient. In some embodiments, the gradient is a salt gradient. In some embodiments, the gradient is a linear salt gradient. In some embodiments, the linear salt gradient comprises between about 0 mM and about 500 mM NaCl. In some embodiments, the linear salt gradient comprises between about 5 mM and about 500 mM NaCl. In some embodiments, the linear salt gradient comprises between about 5 mM and about 200 mM NaCl. In some embodiments, the linear salt gradient comprises between about 10 mM and about 200 mM NaCl. In some embodiments, the linear salt gradient comprises between about 10 mM and about 120 mM NaCl.

In some embodiment, the linear salt gradient is applied to the anion exchange chromatography media (e.g., monolith column) in a volume of between about 5 CV and about 100 CV. In some embodiments, the linear salt gradient is applied in a volume of between about 20 CV and about 80 CV. In some embodiments, the linear salt gradient is applied in a volume of between about 30 CV and about 70 CV. In some embodiments, the linear salt gradient is applied in a volume of between about 40 CV and about 60 CV. In some embodiments, the linear salt gradient is applied in a volume of about 40 CV. In some embodiments, the linear salt gradient is applied in a volume of about 50 CV. In some embodiments, the linear salt gradient is applied in a volume of about 60 CV.

In some embodiment, the linear salt gradient is applied to the anion exchange chromatography media (e.g., monolith column) at a flow rate of between about 0.2 CV/min and about 5 CV/min. In some embodiment, the linear salt gradient is applied to the anion exchange chromatography media at a flow rate of between about 0.5 CV/min and about 1.25 CV/min.

In some embodiments, the rAAV particles bound to the anion exchange chromatography media (e.g., monolith column) are eluted with a liner salt gradient comprising between about 10 mM and about 200 mM NaCl, wherein the gradient is applied in a volume of between about 40 CV and about 60 CV. In some embodiments, the linear salt gradient is applied in a volume of about 40 CV. In some embodiments, the linear salt gradient is applied in a volume of about 50 CV. In some embodiments, the linear salt gradient is applied in a volume of about 60 CV. In some embodiment, the linear salt gradient is applied to the anion exchange chromatography media at a flow rate of between about 0.5 CV/min and about 1.25 CV/min.

In some embodiments, the feed composition comprises rAAV particles that were purified by affinity chromatography using POROS™ CaptureSelect™ AAVX affinity resin, POROS™ CaptureSelect™ AAV9 affinity resin, or POROS™ CaptureSelect™ AAV8 affinity resin. In some embodiments, the feed composition comprises rAAV particles that were purified by affinity chromatography using AVB Sepharose resin. In some embodiments, the feed composition comprises rAAV particles that were purified by heparin affinity chromatography using, for example, POROS™ 50 HE or Heparin Sepharose resin. In some embodiments, the feed composition comprises a composition, e.g., eluate, produced by the affinity chromatography.

In some embodiments, the composition, e.g., eluate, produced by affinity chromatography is treated before contacting it with an anion exchange chromatography media (e.g., monolith column). In some embodiments, pretreating comprises adding a salt. In some embodiments, the pretreating comprises adding a K⁺ or Mg²⁺ salt. In some embodiments, pretreating comprises adding a K⁺ and a Mg²⁺ salt.

In some embodiments, pretreating comprises adding a K⁺ salt to a final concentration of between about 0.2 mM and about 50 mM. In some embodiments, pretreating comprises adding a K⁺ salt to a final concentration of between about 0.5 mM and about 10 mM. In some embodiments, pretreating comprises adding a K⁺ salt to a final concentration of about 1 mM. In some embodiments, the pretreating comprises adding a Mg²⁺ salt to a final concentration of between about 0.2 mM and about 50 mM. In some embodiments, the pretreating comprises adding a Mg²⁺ salt to a final concentration of between about 0.5 mM and about 10 mM. In some embodiments, the pretreating comprises adding a Mg²⁺ salt to a final concentration of about 1 mM. In some embodiments, the pretreating comprises adding a Mg²⁺ salt to a final concentration of about 2.5 mM. In some embodiments, the salt is KCl. In some embodiments, the salt is MgCl₂. In some embodiments, pretreating comprises adding a load dilution buffer comprising between about 0.5 mM and about 10 mM K⁺ and between about 0.5 mM and about 10 mM Mg²⁺. In some embodiments, the load dilution buffer comprises about 2 mM K⁺ and about 5 mM Mg²⁺. In some embodiments, the load dilution buffer comprises about 1 mM K⁺ and about 2.5 mM Mg²⁺. In some embodiments, the load dilution buffer comprises about 2 mM K⁺ and about 2 mM Mg²⁺. In some embodiments, the load dilution buffer comprises about 1 mM K⁺ and about 1 mM Mg²⁺.

In some embodiments, pretreating comprises adjusting pH. In some embodiments, pretreating comprises adjusting pH. In some embodiments, pretreating comprises adjusting pH to between about 7.0 and about 10.2. In some embodiments, pretreating comprises adjusting pH to between about 8.6 and about 9.5. In some embodiments, pretreating comprises adjusting pH to between about 8.2 and about 8.6 or to between about 9.1 and about 9.5. In some embodiments, pretreating comprises adjusting pH to about 8.4. In some embodiments, pretreating comprises adjusting pH to about 9.3. In some embodiments, the composition, e.g., eluate, produced by affinity chromatography is not pre-treated before contacting it with an anion exchange chromatography media (e.g., monolith column).

In some embodiments, the feed composition comprises a composition, e.g., eluate, produced by affinity chromatography, the rAAV particles comprise an AAV capsid serotype of AAV-8, and pretreating comprises adding a K⁺ salt to a final concentration of about 1 mM, adding a Mg²⁺ salt to a final concentration of about 2.5 mM, and adjusting pH to about 8.4.

In some embodiments, the feed composition comprises a composition, e.g., eluate, produced by affinity chromatography, the rAAV particles comprise an AAV capsid serotype of AAV-9, and pretreating comprises adding a K⁺ salt to a final concentration of about 1 mM, adding a Mg²⁺ salt to a final concentration of about 1 mM, and adjusting pH to about 9.3.

In some embodiments, the impurity comprises product-related impurities, for example, inactive vector forms, empty or partially filled viral capsids, aggregated viral particles or capsids, mis-folded viral capsids, degraded viral particles. In some embodiments, the impurity comprises empty viral capsids and aggregated viral particles or capsids.

In some embodiments, the provided methods separate the isolated rAAV particles and the impurity. In some embodiments, the isolated rAAV particles comprise less than about 90% of empty viral capsids. In some embodiments, the isolated rAAV particles comprise less than about 80% of empty viral capsids. In some embodiments, the isolated rAAV particles comprise less than about 70% of empty viral capsids. In some embodiments, the isolated rAAV particles comprise less than about 60% of empty viral capsids. In some embodiments, the isolated rAAV particles comprise less than about 50% of empty viral capsids. In some embodiments, the isolated rAAV particles comprise less than about 40% of empty viral capsids. In some embodiments, the isolated rAAV particles comprise less than about 30% of empty viral capsids. In some embodiments, the isolated rAAV particles comprise less than about 20% of empty viral capsids. In some embodiments, the isolated rAAV particles comprise less than about 15% of empty viral capsids. In some embodiments, the isolated rAAV particles comprise less than about 10% of empty viral capsids. In some embodiments, the isolated rAAV particles comprise less than about 9% of empty viral capsids. In some embodiments, the isolated rAAV particles comprise less than about 8% of empty viral capsids. In some embodiments, the isolated rAAV particles comprise less than about 7% of empty viral capsids. In some embodiments, the isolated rAAV particles comprise less than about 6% of empty viral capsids. In some embodiments, the isolated rAAV particles comprise less than about 5% of empty viral capsids. In some embodiments, the isolated rAAV particles comprise less than about 4% of empty viral capsids. In some embodiments, the isolated rAAV particles comprise less than about 3% of empty viral capsids. In some embodiments, the isolated rAAV particles comprise less than about 2% of empty viral capsids. In some embodiments, the isolated rAAV particles comprise less than about 1% of empty viral capsids.

In some embodiments, at least about 10% of the viral capsids in the eluate are intact rAAV particles. In some embodiments, at least about 20% of the viral capsids in the eluate are intact rAAV particles. In some embodiments, at least about 30% of the viral capsids in the eluate are intact rAAV particles. In some embodiments, at least about 40% of the viral capsids in the eluate are intact rAAV particles. In some embodiments, at least about 50% of the viral capsids in the eluate are intact rAAV particles. In some embodiments, at least about 60% of the viral capsids in the eluate are intact rAAV particles. In some embodiments, at least about 70% of the viral capsids in the eluate are intact rAAV particles. In some embodiments, at least about 80% of the viral capsids in the eluate are intact rAAV particles. In some embodiments, at least about 90% of the viral capsids in the eluate are intact rAAV particles. In some embodiments, at least about 95% of the viral capsids in the eluate are intact rAAV particles. In some embodiments, at least about 97% of the viral capsids in the eluate are intact rAAV particles. In some embodiments, at least about 98% of the viral capsids in the eluate are intact rAAV particles. In some embodiments, at least about 99% of the viral capsids in the eluate are intact rAAV particles.

In some embodiments, the isolated rAAV particles comprise less than about 20% of aggregated viral particles or capsids. In some embodiments, the isolated rAAV particles comprise less than about 15% of aggregated viral particles or capsids. In some embodiments, the isolated rAAV particles comprise less than about 10% of aggregated viral particles or capsids. In some embodiments, the isolated rAAV particles comprise less than about 9% of aggregated viral particles or capsids. In some embodiments, the isolated rAAV particles comprise less than about 8% of aggregated viral particles or capsids. In some embodiments, the isolated rAAV particles comprise less than about 7% of aggregated viral particles or capsids. In some embodiments, the isolated rAAV particles comprise less than about 6% of aggregated viral particles or capsids. In some embodiments, the isolated rAAV particles comprise less than about 5% of aggregated viral particles or capsids. In some embodiments, the isolated rAAV particles comprise less than about 4% of aggregated viral particles or capsids. In some embodiments, the isolated rAAV particles comprise less than about 3% of aggregated viral particles or capsids. In some embodiments, the isolated rAAV particles comprise less than about 2% of aggregated viral particles or capsids. In some embodiments, the isolated rAAV particles comprise less than about 1% of aggregated viral particles or capsids.

The provided methods produce isolated rAAV particles without significant losses of rAAV. In some embodiments, the yield of rAAV particles is at least about 40%. In some embodiments, the yield of rAAV particles is at least about 50%. In some embodiments, the yield of rAAV particles is at least about 60%. In some embodiments, the yield of rAAV particles is at least about 70%. In some embodiments, the yield of rAAV particles is at least about 75%. In some embodiments, the yield of rAAV particles is at least about 80%. In some embodiments, the yield of rAAV particles is at least about 85%. In some embodiments, the yield of rAAV particles is at least about 90%. In some embodiments, the yield of rAAV particles is at least about 95%. In some embodiments, the yield of rAAV particles is at least about 96%. In some embodiments, the yield of rAAV particles is at least about 97%. In some embodiments, the yield of rAAV particles is at least about 98%. In some embodiments, the yield of rAAV particles is at least about 99%. In one embodiment, the yield is genome copy (GC) yield.

In some embodiments, inclusion of a monovalent cation ($K^+$, $Rb^+$, or $Cs^+$) and divalent cation (e.g., $Mg^{2+}$, $Ca^{2+}$, or $Zn^{2+}$) in the chromatography buffers, e.g., fed composition, equilibration buffer, load dilution buffer, wash buffer, elution buffer, increases the yield of rAAV particles. In some embodiments, inclusion of a monovalent cation ($K^+$, $Rb^+$, or $Cs^+$) and divalent cation (e.g., $Mg^{2+}$, $Ca^{2+}$, or $Zn^{2+}$) in the chromatography buffers increases genome copy (GC) yield by about between 5% and 35%. In some embodiments, the yield is increased by between about 10% and about 30%. In some embodiments, the yield is increased by about 10%. In some embodiments, the yield is increased by about 15%. In some embodiments, the yield is increased by about 20%. In some embodiments, the yield is increased by about 25%. In some embodiments, the yield is increased by about 30%.

In some embodiments, inclusion of a $K^+$ and $Mg^{2+}$ in the chromatography buffers, e.g., fed composition, equilibration buffer, load dilution buffer, wash buffer, elution buffer, increases the yield of rAAV particles. In some embodiments, inclusion of a $K^+$ and $Mg^{2+}$ in the chromatography buffers increases genome copy (GC) yield by about between 5% and 35%. In some embodiments, the yield is increased by between about 10% and about 30%. In some embodiments, the yield is increased by about 10%. In some embodiments, the yield is increased by about 15%. In some embodiments, the yield is increased by about 20%. In some embodiments, the yield is increased by about 25%. In some embodiments, the yield is increased by about 30%.

rAAV Particles

The provided methods are suitable for use in the production of any isolated recombinant AAV particles. As such, the rAAV in the feed composition according to the disclosed methods can be of any serotype, modification, or derivative, known in the art, or any combination thereof (e.g., a population of rAAV particles that comprises two or more serotypes, e.g., comprising two or more of rAAV2, rAAV8, and rAAV9 particles) known in the art. In some embodiments, the rAAV particles are AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or other rAAV particles, or combinations of two or more thereof.

In some embodiments, rAAV particles have a capsid protein from an AAV serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16 or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, rAAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise a capsid protein from an AAV capsid serotype selected from AAV1, AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16, or a derivative, modification, or pseudotype thereof. In some embodiments, rAAV particles comprise a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to e.g., VP1, VP2 and/or VP3 sequence of an AAV capsid serotype selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In some embodiments, rAAV particles comprise the capsid of Anc80 or Anc80L65, as described in Zinn et al., 2015, Cell Rep. 12(6): 1056-1068, which is incorporated by reference in its entirety. In certain embodiments, the rAAV particles comprise the capsid with one of the following amino acid insertions: LGETTRP or LALGETTRP, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise the capsid of AAV.7m8, as described in U.S. Pat. Nos. 9,193,956; 9,458,517; and 9,587,282 and US patent application publication no. 2016/0376323, each of which is incorporated herein by reference in its entirety. In some embodiments, rAAV particles comprise any AAV capsid disclosed in U.S. Pat. No. 9,585,971, such as AAV-PHP.B. In some embodiments, rAAV particles comprise any AAV capsid disclosed in U.S. Pat. No. 9,840,719 and WO 2015/013313, such as AAV.Rh74 and RHM4-1, each of which is incorporated herein by reference in its entirety. In some embodiments, rAAV particles comprise any AAV capsid disclosed in WO 2014/172669, such as AAV rh.74, which is incorporated herein by reference in its entirety. In some embodiments, rAAV particles comprise the capsid of AAV2/5, as described in Georgiadis et al., 2016, Gene Therapy 23: 857-862 and Georgiadis et al., 2018, Gene Therapy 25: 450, each of which is incorporated by reference in its entirety. In some embodiments, rAAV particles comprise any AAV capsid disclosed in WO 2017/070491, such as AAV2tYF, which is incorporated herein by reference in its entirety. In some embodiments, rAAV particles comprise the capsids of AAVLK03 or AAV3B, as described in Puzzo et al., 2017, Sci. Transl. Med. 29(9): 418, which is incorporated by reference in its entirety. In some embodiments, rAAV particles comprise any AAV capsid disclosed in U.S. Pat. Nos. 8,628,966; 8,927,514; 9,923,120 and WO 2016/049230, such as HSC1, HSC2, HSC3, HSC4, HSC5, HSC6, HSC7, HSC8, HSC9, HSC10, HSC11, HSC12, HSC13, HSC14, HSC15, or HSC16, each of which is incorporated by reference in its entirety.

In some embodiments, rAAV particles comprise an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in any of the following patents and patent applications, each of which is incorporated herein by reference in its entirety: U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282;

US patent application publication nos. 2015/0374803; 2015/0126588; 2017/0067908; 2013/0224836; 2016/0215024; 2017/0051257; and International Patent Application Nos. PCT/US2015/034799; PCT/EP2015/053335.

In some embodiments, rAAV particles have a capsid protein disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689, (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10), the contents of each of which is herein incorporated by reference in its entirety. In some embodiments, rAAV particles have a capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of an AAV capsid disclosed in Intl. Appl. Publ. No. WO 2003/052051 (see, e.g., SEQ ID NO: 2), WO 2005/033321 (see, e.g., SEQ ID NOs: 123 and 88), WO 03/042397 (see, e.g., SEQ ID NOs: 2, 81, 85, and 97), WO 2006/068888 (see, e.g., SEQ ID NOs: 1 and 3-6), WO 2006/110689 (see, e.g., SEQ ID NOs: 5-38) WO2009/104964 (see, e.g., SEQ ID NOs: 1-5, 7, 9, 20, 22, 24 and 31), WO 2010/127097 (see, e.g., SEQ ID NOs: 5-38), and WO 2015/191508 (see, e.g., SEQ ID NOs: 80-294), and U.S. Appl. Publ. No. 20150023924 (see, e.g., SEQ ID NOs: 1, 5-10).

Nucleic acid sequences of AAV based viral vectors and methods of making recombinant AAV and AAV capsids are taught, for example, in U.S. Pat. Nos. 7,282,199; 7,906,111; 8,524,446; 8,999,678; 8,628,966; 8,927,514; 8,734,809; 9,284,357; 9,409,953; 9,169,299; 9,193,956; 9,458,517; and 9,587,282; US patent application publication nos. 2015/0374803; 2015/0126588; 2017/0067908; 2013/0224836; 2016/0215024; 2017/0051257; International Patent Application Nos. PCT/US2015/034799; PCT/EP2015/053335; WO 2003/052051, WO 2005/033321, WO 03/042397, WO 2006/068888, WO 2006/110689, WO2009/104964, WO 2010/127097, and WO 2015/191508, and U.S. Appl. Publ. No. 20150023924.

The provided methods are suitable for used in the production of recombinant AAV encoding a transgene. In some embodiments, provided herein are rAAV viral vectors encoding an anti-VEGF Fab. In specific embodiments, provided herein are rAAV8-based viral vectors encoding an anti-VEGF Fab. In more specific embodiments, provided herein are rAAV8-based viral vectors encoding ranibizumab. In some embodiments, provided herein are rAAV viral vectors encoding Iduronidase (IDUA). In specific embodiments, provided herein are rAAV9-based viral vectors encoding IDUA. In some embodiments, provided herein are rAAV viral vectors encoding Iduronate 2-Sulfatase (IDS). In specific embodiments, provided herein are rAAV9-based viral vectors encoding IDS. In some embodiments, provided herein are rAAV viral vectors encoding a low-density lipoprotein receptor (LDLR). In specific embodiments, provided herein are rAAV8-based viral vectors encoding LDLR. In some embodiments, provided herein are rAAV viral vectors encoding tripeptidyl peptidase 1 (TPP1) protein. In specific embodiments, provided herein are rAAV9-based viral vectors encoding TPP.

In additional embodiments, rAAV particles comprise a pseudotyped AAV capsid. In some embodiments, the pseudotyped AAV capsids are rAAV2/8 or rAAV2/9 pseudotyped AAV capsids. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In some embodiments, the capsid protein is a chimeric of 2 or more AAV capsid proteins from AAV serotypes selected from AAV1, AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, or AAV.HSC16.

In certain embodiments, a single-stranded AAV (ssAAV) can be used. In certain embodiments, a self-complementary vector, e.g., scAAV, can be used (see, e.g., Wu, 2007, Human Gene Therapy, 18(2):171-82, McCarty et al, 2001, Gene Therapy, Vol. 8, Number 16, Pages 1248-1254; and U.S. Pat. Nos. 6,596,535; 7,125,717; and 7,456,683, each of which is incorporated herein by reference in its entirety).

In some embodiments, rAAV particles in the clarified feed comprise a capsid protein from an AAV capsid serotype selected from AAV-8 or AAV-9. In some embodiments, the rAAV particles have an AAV capsid serotype of AAV-1 or a derivative, modification, or pseudotype thereof. In some embodiments, the rAAV particles have an AAV capsid serotype of AAV-4 or a derivative, modification, or pseudotype thereof. In some embodiments, the rAAV particles have an AAV capsid serotype of AAV-5 or a derivative, modification, or pseudotype thereof. In some embodiments, the rAAV particles have an AAV capsid serotype of AAV-8 or a derivative, modification, or pseudotype thereof. In some embodiments, the rAAV particles have an AAV capsid serotype of AAV-9 or a derivative, modification, or pseudotype thereof.

In some embodiments, rAAV particles comprise a capsid protein that is a derivative, modification, or pseudotype of AAV-8 or AAV-9 capsid protein. In some embodiments, rAAV particles comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-8 capsid protein.

In some embodiments, rAAV particles comprise a capsid protein that is a derivative, modification, or pseudotype of AAV-9 capsid protein. In some embodiments, rAAV particles comprise a capsid protein that has an AAV-8 capsid protein at least 80% or more identical, e.g., 85%, 85%, 87%, 88%, 89%, 90%, 91%, 92%, 93%, 94%, 95%, 96%, 97%, 98%, 99%, 99.5%, etc., i.e. up to 100% identical, to the VP1, VP2 and/or VP3 sequence of AAV-9 capsid protein.

In additional embodiments, rAAV particles comprise a mosaic capsid. Mosaic AAV particles are composed of a mixture of viral capsid proteins from different serotypes of AAV. In some embodiments, rAAV particles comprise a mosaic capsid containing capsid proteins of a serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, rAAV particles comprise a mosaic capsid containing capsid proteins of a serotype selected from AAV-1, AAV-2, AAV-5, AAV-6, AAV-7, AAV-8, AAV-9, AAV-10, AAVrh.8, and AAVrh.10.

In additional embodiments, rAAV particles comprise a pseudotyped rAAV particle. In some embodiments, the pseudotyped rAAV particle comprises (a) a nucleic acid vector comprising AAV ITRs and (b) a capsid comprised of capsid proteins derived from AAVx (e.g., AAV-1, AAV-3, AAV-4, AAV-5, AAV-6, AAV-7, AAV-8, AAV-9, AAV-10 AAV-11, AAV-12, AAV-13, AAV-14, AAV-15 and AAV-16). In additional embodiments, rAAV particles comprise a pseudotyped rAAV particle comprised of a capsid protein of an AAV serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In additional embodiments, rAAV particles comprise a pseudotyped rAAV particle containing AAV-8 capsid protein. In additional embodiments, rAAV particles comprise a pseudotyped rAAV particle is comprised of AAV-9 capsid protein. In some embodiments, the pseudotyped rAAV8 or rAAV9 particles are rAAV2/8 or rAAV2/9 pseudotyped particles. Methods for producing and using pseudotyped rAAV particles are known in the art (see, e.g., Duan et al., J. Virol., 75:7662-7671 (2001); Halbert et al., J. Virol., 74:1524-1532 (2000); Zolotukhin et al., Methods 28:158-167 (2002); and Auricchio et al., Hum. Molec. Genet. 10:3075-3081, (2001).

In additional embodiments, rAAV particles comprise a capsid containing a capsid protein chimeric of two or more AAV capsid serotypes. In further embodiments, the capsid protein is a chimeric of 2 or more AAV capsid proteins from AAV serotypes selected from AAV1, AAV2, rAAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, rAAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In further embodiments, the capsid protein is a chimeric of 2 or more AAV capsid proteins from AAV serotypes selected from AAV-1, AAV-2, AAV-5, AAV-6, AAV-7, AAV-8, AAV-9, AAV-10, AAVrh.8, and AAVrh.10.

In some embodiments, the rAAV particles comprise an AAV capsid protein chimeric of AAV-8 capsid protein and one or more AAV capsid proteins from an AAV serotype selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16. In some embodiments, the rAAV particles comprise an AAV capsid protein chimeric of AAV-8 capsid protein and one or more AAV capsid proteins from an AAV serotype selected from AAV-1, AAV-2, AAV-5, AAV-6, AAV-7, AAV-9, AAV-10, AAVrh.8, and AAVrh.10.

In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AAV6, AAV7, AAV8, AAV9, AAV10, AAV-11, AAV-12, AAV-13, AAV-14, AAV-15 and AAV-16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16.

In some embodiments, the rAAV particles comprise an AAV capsid protein chimeric of AAV-9 capsid protein the capsid protein of one or more AAV capsid serotypes selected from AAV1, AAV2, AAV3, AAV4, AAV5, AA6, AAV7, AAV8, AAV9, AAVrh.8, and AAVrh.10.

Methods for Isolating rAAV

Methods of purification using an anion exchange chromatography resin (e.g., monolith anion exchange chromatography resin or an AEX chromatography resin comprising quaternary amine ligand) disclosed herein (e.g., the method of any one of [1]-[55]) can be used in combination with upstream processing, downstream processing, or upstream and downstream processing methods to isolate rAAV particles.

The feed composition for a method of isolating rAAV particles using an anion exchange chromatography resin (e.g., monolith anion exchange chromatography resin or an AEX chromatography resin comprising quaternary amine ligand) prepared according to the disclosed methods (e.g., the method of any one of [1]-[55]) can be generated using methods known in the art. In some embodiments, methods of isolating rAAV particles disclosed herein comprise generating the feed composition by a method comprising upstream processing such as, for example, harvest of a cell culture e.g. cell culture supernatant or cell lysate or both, clarification of the harvested cell culture or cell culture supernatant (e.g., by centrifugation or depth filtration), tangential flow filtration, affinity chromatography, cation exchange chromatography, size exclusion chromatography, hydrophobic interaction chromatography, sterile filtration, or any combination(s) thereof. In some embodiments, upstream processing includes at least 2, at least 3, or at least 4 of: harvest of a cell culture or cell culture supernatant, clarification of the harvested cell culture or cell culture supernatant (e.g., by centrifugation or depth filtration), tangential flow filtration, affinity chromatography, cation exchange chromatography, size exclusion chromatography, hydrophobic interaction chromatography, sterile filtration. In some embodiments, upstream processing comprises harvest of a cell culture or cell culture supernatant, clarification of the harvested cell culture or cell culture supernatant (e.g., by depth filtration), sterile filtration, tangential flow filtration, and affinity chromatography. In some embodiments, upstream processing comprises clarification of a harvested cell culture or cell culture supernatant, sterile filtration, tangential flow filtration, and affinity chromatography. In some embodiments, upstream processing comprises clarification of a harvested cell culture or cell culture supernatant by depth filtration, sterile filtration, tangential flow filtration, and affinity chromatography. In some embodiments, clarification of the harvested cell culture or cell culture supernatant comprises sterile filtration. In some embodiments, upstream processing does not include centrifugation. In some embodiments, the rAAV particles comprise a capsid protein of the AAV-8 serotype. In some embodiments, the rAAV particles comprise a capsid protein of the AAV-9 serotype.

The eluate from an anion exchange chromatography resin (e.g., monolith column) comprising isolated rAAV particles produced according to the disclosed methods (e.g., the method of any one of [1]-[55]) can be further processed using methods known in the art. In some embodiments, methods of isolating rAAV particles disclosed herein comprise processing the eluate by a method comprising downstream processing such as, for example, tangential flow filtration, affinity chromatography, size exclusion chromatography, cation exchange chromatography, hydroxylapatite chromatography, and hydrophobic interaction chromatography. In some embodiments, downstream processing includes at least 2, at least 3, or at least 4 of: tangential flow filtration, affinity chromatography, anion exchange chromatography, hydrophobic interaction chromatography, size exclusion chromatography, or sterile filtration. In some embodiments, downstream processing includes tangential flow filtration. In some embodiments, downstream processing includes sterile filtration. In further embodiments, downstream processing includes tangential flow filtration and sterile filtration. In some embodiments, the rAAV particles comprise a capsid protein of the AAV-8 serotype. In some embodiments, the rAAV particles comprise a capsid protein of the AAV-9 serotype.

In some embodiments, a method of isolating rAAV particles disclosed herein comprises harvest of a cell culture or cell culture supernatant, clarification of the harvested cell culture or cell culture supernatant (e.g., by depth filtration), a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises harvest of a cell culture or cell culture supernatant, clarification of the harvested cell culture or cell culture supernatant (e.g., by depth filtration), a first sterile filtration, affinity chromatography, anion exchange chromatography (e.g., monolith anion exchange chromatography or AEX chromatography using a quaternary amine ligand), a tangential flow filtration, and a second sterile filtration. In some embodiments, a method of isolating rAAV particles disclosed herein comprises clarification of a harvested cell culture or cell culture supernatant, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises clarification of a harvested cell culture or cell culture supernatant, a first sterile filtration, affinity chromatography, anion exchange chromatography (e.g., monolith anion exchange chromatography or AEX chromatography using a quaternary amine ligand), tangential flow filtration, and a second sterile filtration. In some embodiments, a method of isolating rAAV particles disclosed herein comprises clarification of a harvested cell culture or cell culture supernatant by depth filtration, a first sterile filtration, a first tangential flow filtration, affinity chromatography, anion exchange chromatography (e.g., monolith anion exchange chromatography or AEX chromatography using a quaternary amine ligand), a second tangential flow filtration, and a second sterile filtration. In some embodiments, a method of isolating rAAV particles disclosed herein comprises clarification of a harvested cell culture or cell culture supernatant by depth filtration, a first sterile filtration, affinity chromatography, anion exchange chromatography (e.g., monolith anion exchange chromatography or AEX chromatography using a quaternary amine ligand), tangential flow filtration, and a second sterile filtration. In some embodiments, the method does not include centrifugation. In some embodiments, clarification of the harvested cell culture or cell culture supernatant comprises sterile filtration. In some embodiments, the rAAV particles comprise a capsid protein of the AAV-8 serotype. In some embodiments, the rAAV particles comprise a capsid protein of the AAV-9 serotype.

Numerous methods are known in the art for production of rAAV particles, including transfection, stable cell line production, and infectious hybrid virus production systems which include Adenovirus-AAV hybrids, herpesvirus-AAV hybrids and baculovirus-AAV hybrids. rAAV production cultures for the production of rAAV virus particles all require; (1) suitable host cells, including, for example, human-derived cell lines such as HeLa, A549, or HEK293 cells and their derivatives (HEK293T cells, HEK293F cells), mammalian cell lines such as Vero, or insect-derived cell lines such as SF-9 in the case of baculovirus production systems; (2) suitable helper virus function, provided by wild type or mutant adenovirus (such as temperature sensitive adenovirus), herpes virus, baculovirus, or a plasmid construct providing helper functions; (3) AAV rep and cap genes and gene products; (4) a transgene (such as a therapeutic transgene) flanked by AAV ITR sequences; and (5) suitable media and media components to support rAAV production. Suitable media known in the art may be used for the production of rAAV vectors. These media include, without limitation, media produced by Hyclone Laboratories and JRH including Modified Eagle Medium (MEM), Dulbecco's Modified Eagle Medium (DMEM), and Sf-900 II SFM media as described in U.S. Pat. No. 6,723,551, which is incorporated herein by reference in its entirety.

rAAV production cultures can routinely be grown under a variety of conditions (over a wide temperature range, for varying lengths of time, and the like) suitable to the particular host cell being utilized. As is known in the art, rAAV production cultures include attachment-dependent cultures which can be cultured in suitable attachment-dependent vessels such as, for example, roller bottles, hollow fiber filters, microcarriers, and packed-bed or fluidized-bed bioreactors. rAAV vector production cultures may also include suspension-adapted host cells such as HeLa, HEK293, Vero, and its derivatives, and SF-9 cells which can be cultured in a variety of ways including, for example, spinner flasks, stirred tank bioreactors, and disposable systems such as the Wave bag system. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety.

Recombinant AAV particles can be harvested from rAAV production cultures by harvest of the production culture comprising host cells or by harvest of the spent media from the production culture, provided the cells are cultured under conditions known in the art to cause release of rAAV particles into the media from intact host cells. Recombinant AAV particles can also be harvested from rAAV production cultures by lysis of the host cells of the production culture. Suitable methods of lysing cells are also known in the art and include for example multiple freeze/thaw cycles, sonication, microfluidization, and treatment with chemicals, such as detergents and/or proteases.

In some embodiments, the rAAV production culture comprises a high density cell culture. In some embodiments, the culture has a total cell density of between about $1\times10E+06$ cells/ml and about $30\times10E+06$ cells/ml. In some embodiments, more than about 50% of the cells are viable cells. In some embodiments, the cells are HeLa cells, HEK293 cells, HEK293 derived cells (e.g., HEK293T cells, HEK293F cells), Vero cells, or SF-9 cells. In further embodiments, the cells are HEK293 cells. In further embodiments, the cells are HEK293 cells adapted for growth in suspension culture.

In additional embodiments of the provided method the rAAV production culture comprises a suspension culture comprising rAAV particles. Numerous suspension cultures are known in the art for production of rAAV particles, including for example, the cultures disclosed in U.S. Pat. Nos. 6,995,006, 9,783,826, and in U.S. Pat. Appl. Pub. No. 20120122155, each of which is incorporated herein by reference in its entirety. In some embodiments, the suspension culture comprises a culture of mammalian cells or insect cells. In some embodiments, the suspension culture comprises a culture of HeLa cells, HEK293 cells, HEK293 derived cells (e.g., HEK293T cells, HEK293F cells), Vero cells, CHO cells, CHO—K1 cells, EB66 cells, BSC cells, HepG2 cells, LLC-MK cells, CV-1 cells, COS cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, NS-1 cells, MRC-5 cells, WI-38 cells, BHK cells, 3T3 cells, 293 cells, RK cells, Per.C6 cells, chicken embryo cells or SF-9 cells. In some embodiments, the suspension culture comprises a culture of HEK293 cells.

In some embodiments of the methods disclosed herein large volumes of cell culture or cell culture supernatant feed can be present (e.g., during the commercial manufacturing processes). In some embodiments the methods disclosed herein are suitable for the processing of a large volume of cell culture or cell culture supernatant feed comprising rAAV particles. The term "large volume" refers to volumes associated with the commercial and/or industrial production of rAAV particles. In some embodiments, the term "large volume" refers to between about 20 liters and about 20000 liters, between about 50 liters and about 20000 liters, between about 100 liters and about 20000 liters, between about 500 liters and about 20000 liters, between about 1000 liters and about 20000 liters, between about 20 liters and about 5000 liters, between about 50 liters and about 5000 liters, between about 100 liters and about 3000 liters, between about 500 liters and about 3000 liters, between about 1500 liters and about 2500 liters. In some embodiments, the term "large volume" refers to about 2000 liters. In some embodiments, the term "large volume" refers to about 200 liters. In some embodiments, the term "large volume" refers to about 500 liters. In some embodiments, the term "large volume" refers to about 1000 liters. In some embodiments, the term "large volume" refers to about 1500 liters. In some embodiments, the term "large volume" refers to about 2000 liters. In some embodiments, the term "large volume" refers to about 2500 liters. In some embodiments, the term "large volume" refers to about 3000 liters. In some embodiments, the term "large volume" refers to about 5000 liters. In some embodiments, the term "large volume" refers to about 10000 liters. In some embodiments, the term "large volume" refers to about 15000 liters. In some embodiments, the term "large volume" refers to about 20000 liters. In some embodiments, the term "large volume" refers to between about 10 liters and 1000 liters, between about 10 liters and 100 liters, between about 20 liters and 500 liters, between about 50 liters and 500 liters, between about 100 liters and 1000 liters, or between about 100 liters and 500 liters.

At harvest, rAAV production cultures can contain one or more of the following: (1) host cell proteins; (2) host cell DNA; (3) plasmid DNA; (4) helper virus; (5) helper virus proteins; (6) helper virus DNA; and (7) media components including, for example, serum proteins, amino acids, transferrins and other low molecular weight proteins. rAAV production cultures can further contain product-related impurities, for example, inactive vector forms, empty viral capsids, aggregated viral particles or capsids, mis-folded viral capsids, degraded viral particle.

In some embodiments, the rAAV production culture harvest is clarified to remove host cell debris. In some embodiments, the production culture harvest is clarified by filtration through a series of depth filters. Clarification can also be achieved by a variety of other standard techniques known in the art, such as, centrifugation or filtration through any cellulose acetate filter of 0.2 mm or greater pore size known in the art. In some embodiments, clarification of the harvested cell culture or cell culture supernatant comprises sterile filtration. In some embodiments, the production culture harvest is clarified by centrifugation. In some embodiments, clarification of the production culture harvest does not included centrifugation.

In some embodiments, harvested cell culture or cell culture supernatant is clarified using filtration. In some embodiments, clarification of the harvested cell culture or cell culture supernatant comprises depth filtration. In some embodiments, clarification of the harvested cell culture or cell culture supernatant further comprises depth filtration and sterile filtration. In some embodiments, harvested cell culture or cell culture supernatant is clarified using a filter train comprising one or more different filtration media. In some embodiments, the filter train comprises a depth filtration media. In some embodiments, the filter train comprises one or more depth filtration media. In some embodiments, the filter train comprises two depth filtration media. In some embodiments, the filter train comprises a sterile filtration media. In some embodiments, the filter train comprises 2 depth filtration media and a sterile filtration media. In some embodiments, the depth filter media is a porous depth filter. In some embodiments, the filter train comprises Clarisolve® 20MS, Millistak+® COHC, and a sterilizing grade filter media. In some embodiments, the filter train comprises Clarisolve® 20MS, Millistak+® COHC, and Sartopore® 2 XLG 0.2 µm. In some embodiments, the harvested cell culture or cell culture supernatant is pretreated before contacting it with the depth filter. In some embodiments, the pretreating comprises adding a salt to the harvested cell culture or cell culture supernatant. In some embodiments, the pretreating comprises adding a chemical flocculent to the harvested cell culture or cell culture supernatant. In some embodiments, the harvested cell culture or cell culture supernatant is not pre-treated before contacting it with the depth filter.

In some embodiments, the production culture harvest is clarified by filtration are disclosed in International Application No. PCT/US2019/29539, filed on Apr. 27, 2019, titled "SCALABLE CLARIFICATION PROCESS FOR RECOMBINANT AAV PRODUCTION," which is incorporated herein by reference in its entirety.

In some embodiments, the rAAV production culture harvest is treated with a nuclease (e.g., Benzonase®) or endonuclease (e.g., endonuclease from *Serratia marcescens*) to digest high molecular weight DNA present in the production culture. The nuclease or endonuclease digestion can routinely be performed under standard conditions known in the art. For example, nuclease digestion is performed at a final concentration of e.g. 1-100 U/mL of Benzonase® at a temperature ranging from ambient to 37° C. for a period of 30 minutes to several hours.

Sterile filtration encompasses filtration using a sterilizing grade filter media. In some embodiments, the sterilizing grade filter media is a 0.2 or 0.22 µm pore filter. In some embodiments, the sterilizing grade filter media comprises polyethersulfone (PES). In some embodiments, the sterilizing grade filter media comprises polyvinylidene fluoride (PVDF). In some embodiments, the sterilizing grade filter media has a hydrophilic heterogeneous double layer design. In some embodiments, the sterilizing grade filter media has a hydrophilic heterogeneous double layer design of a 0.8 µm pre-filter and 0.2 µm final filter membrane. In some embodiments, the sterilizing grade filter media has a hydrophilic heterogeneous double layer design of a 1.2 µm pre-filter and 0.2 µm final filter membrane. In some embodiments, the sterilizing grade filter media is a 0.2 or 0.22 µm pore filter. In further embodiments, the sterilizing grade filter media is a 0.2 µm pore filter. In some embodiments, the sterilizing grade filter media is a Sartopore® 2 XLG 0.2 µm, Durapore™ PVDF Membranes 0.45 µm, or Sartoguard® PES 1.2 µm+0.2 µm nominal pore size combination. In some embodiments, the sterilizing grade filter media is a Sartopore® 2 XLG 0.2 µm.

In some embodiments, the clarified feed is concentrated via tangential flow filtration ("TFF") before being applied to a chromatographic medium, for example, affinity chromatography medium. Large scale concentration of viruses using TFF ultrafiltration has been described by Paul et al., Human Gene Therapy 4:609-615 (1993). TFF concentration of the clarified feed enables a technically manageable volume of clarified feed to be subjected to chromatography and allows for more reasonable sizing of columns without the need for lengthy recirculation times. In some embodiments, the clarified feed is concentrated between at least two-fold and at least ten-fold. In some embodiments, the clarified feed is concentrated between at least ten-fold and at least twenty-fold. In some embodiments, the clarified feed is concentrated between at least twenty-fold and at least fifty-fold. In some embodiments, the clarified feed is concentrated about twenty-fold. One of ordinary skill in the art will also recognize that TFF can also be used to remove small molecule impurities (e.g., cell culture contaminants comprising media components, serum albumin, or other serum proteins) form the clarified feed via diafiltration. In some embodiments, the clarified feed is subjected to diafiltration to remove small molecule impurities. In some embodiments, the diafiltration comprises the use of between about 3 and about 10 diafiltration volume of buffer. In some embodiments, the diafiltration comprises the use of about 5 diafiltration volume of buffer. One of ordinary skill in the art will also recognize that TFF can also be used at any step in the purification process where it is desirable to exchange buffers before performing the next step in the purification process. In some embodiments, the methods for isolating rAAV from the clarified feed disclosed herein comprise the use of TFF to exchange buffers.

Affinity chromatography can be used to isolate rAAV particles from a composition. In some embodiments, affinity chromatography is used to isolate rAAV particles from the clarified feed. In some embodiments, affinity chromatography is used to isolate rAAV particles from the clarified feed that has been subjected to tangential flow filtration. Suitable affinity chromatography media are known in the art and include without limitation, AVB Sepharose™, POROS™ CaptureSelect™ AAVX affinity resin, POROS™ CaptureSelect™ AAV9 affinity resin, and POROS™ CaptureSelect™ AAV8 affinity resin. In some embodiments, the affinity chromatography media is POROS™ CaptureSelect™ AAV9 affinity resin. In some embodiments, the affinity chromatography media is POROS™ CaptureSelect™ AAV8 affinity resin. In some embodiments, the affinity chromatography media is POROS™ CaptureSelect™ AAVX affinity resin.

In additional embodiments the disclosure provides compositions comprising isolated recombinant rAAV particles produced by a method disclosed herein. In some embodiment, the composition is a pharmaceutical composition comprising a pharmaceutically acceptable carrier.

As used herein the term "pharmaceutically acceptable means a biologically acceptable formulation, gaseous, liquid or solid, or mixture thereof, which is suitable for one or more routes of administration, in vivo delivery or contact. A "pharmaceutically acceptable" composition is a material that is not biologically or otherwise undesirable, e.g., the material may be administered to a subject without causing substantial undesirable biological effects. Thus, such a pharmaceutical composition may be used, for example in administering rAAV isolated according to the disclosed methods to a subject. Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions. Pharmaceutical compositions can be formulated to be compatible with a particular route of administration or delivery, as set forth herein or known to one of skill in the art. Thus, pharmaceutical compositions include carriers, diluents, or excipients suitable for administration by various routes. Pharmaceutical compositions and delivery systems appropriate for rAAV particles and methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel and Stoklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

In some embodiments, the composition is a pharmaceutical unit dose. A "unit dose" refers to a physically discrete unit suited as a unitary dosage for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dose forms may be within, for example, ampules and vials, which may include a liquid composition, or a composition in a freeze-dried or lyophilized state; a sterile liquid carrier, for example, can be added prior to administration or delivery in vivo. Individual unit dose forms can be included in multi-dose kits or containers. Recombinant vector (e.g., AAV) sequences, plasmids, vector genomes, and recombinant virus particles, and pharmaceutical compositions thereof can be packaged in single or multiple unit dose form for ease of administration and uniformity of dosage. In some embodiments, the composition comprises rAAV particles comprising an AAV capsid protein from an AAV capsid serotype selected from AAV-1, AAV-2, AAV-3, AAV-4, AAV-5, AAV-6, AAV-7, AAV-8, AAV-9, AAV-10, AAV-11, AAV-12, AAV-13, AAV-14, AAV-15 and AAV-16. In some embodiments, the AAV capsid serotype is AAV-8. In some embodiments, the AAV capsid serotype is AAV-9.

EXAMPLES

Example 1. Screening of AEX Resins for AAV8 Purification

Figure 1B:
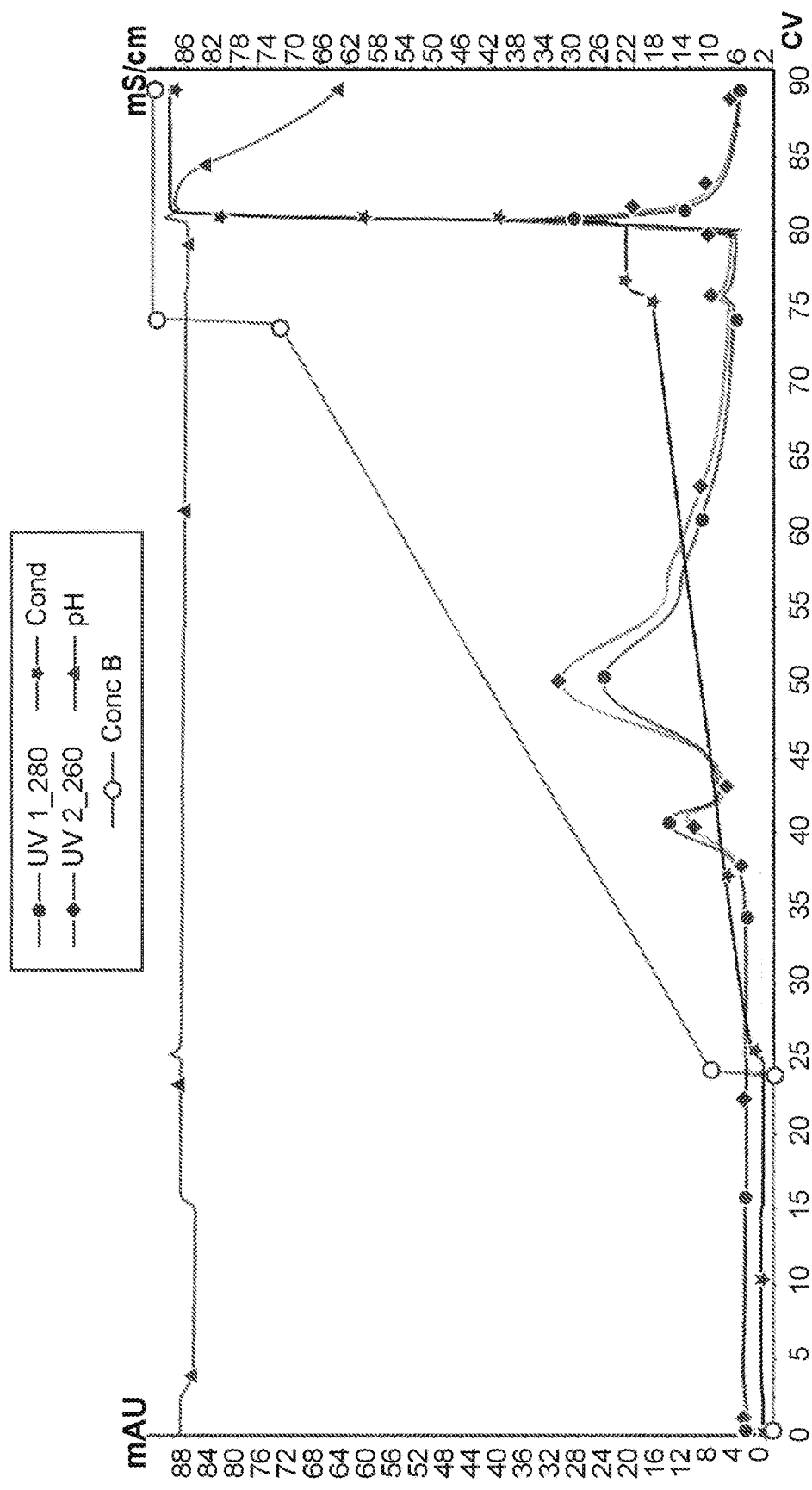
Figure 1C:
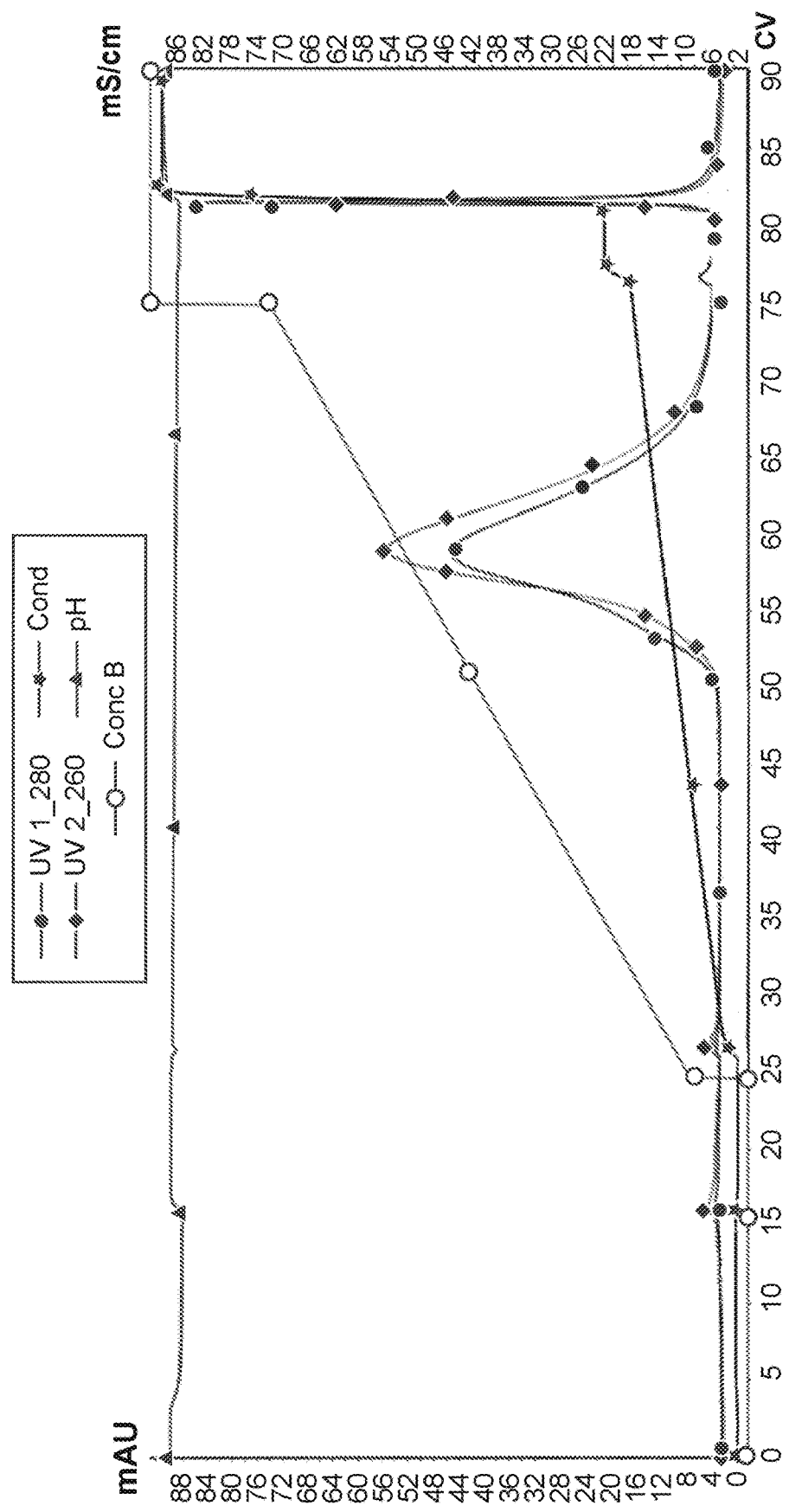
Figure 1D:
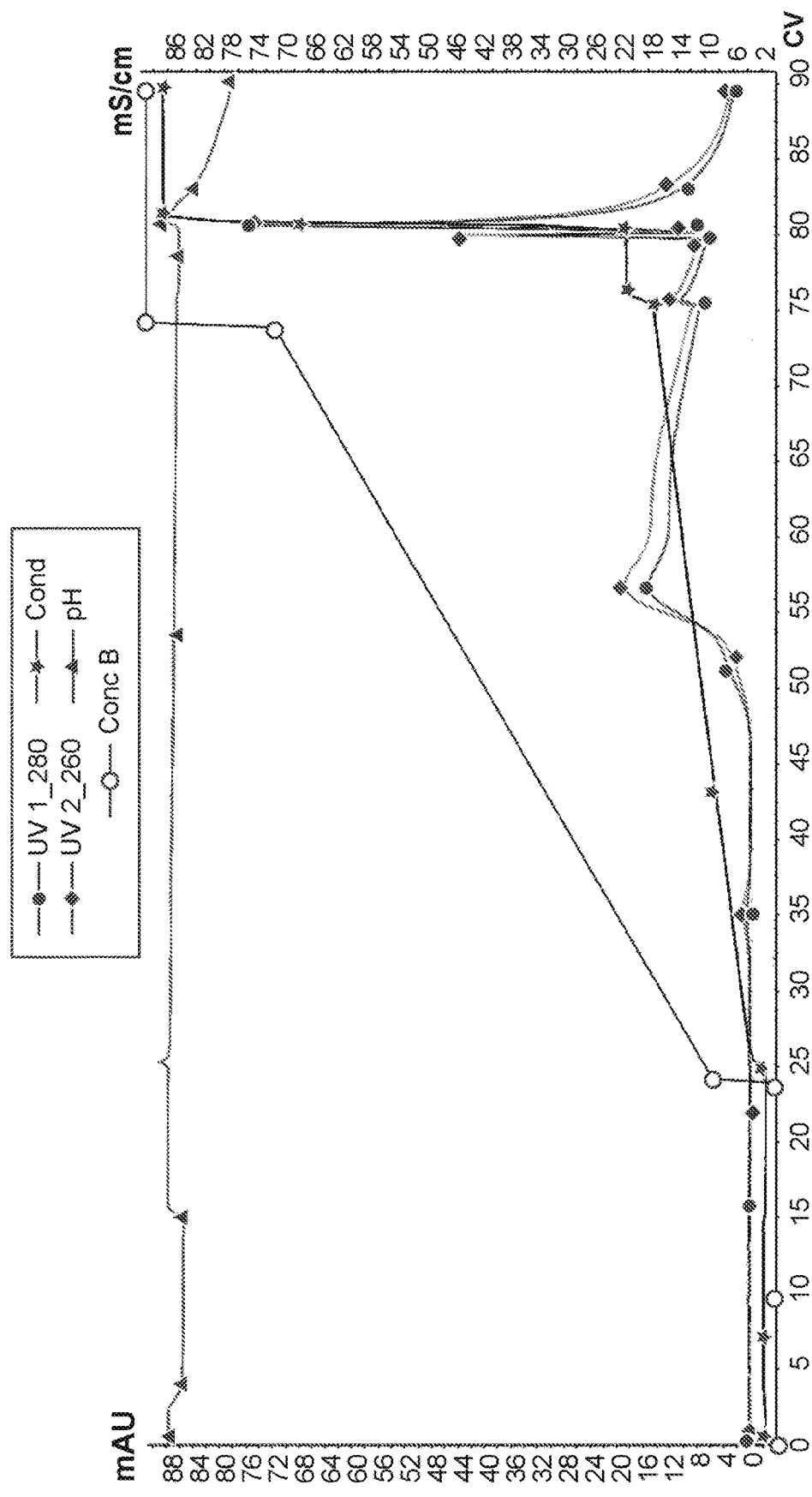
Figure 1E:
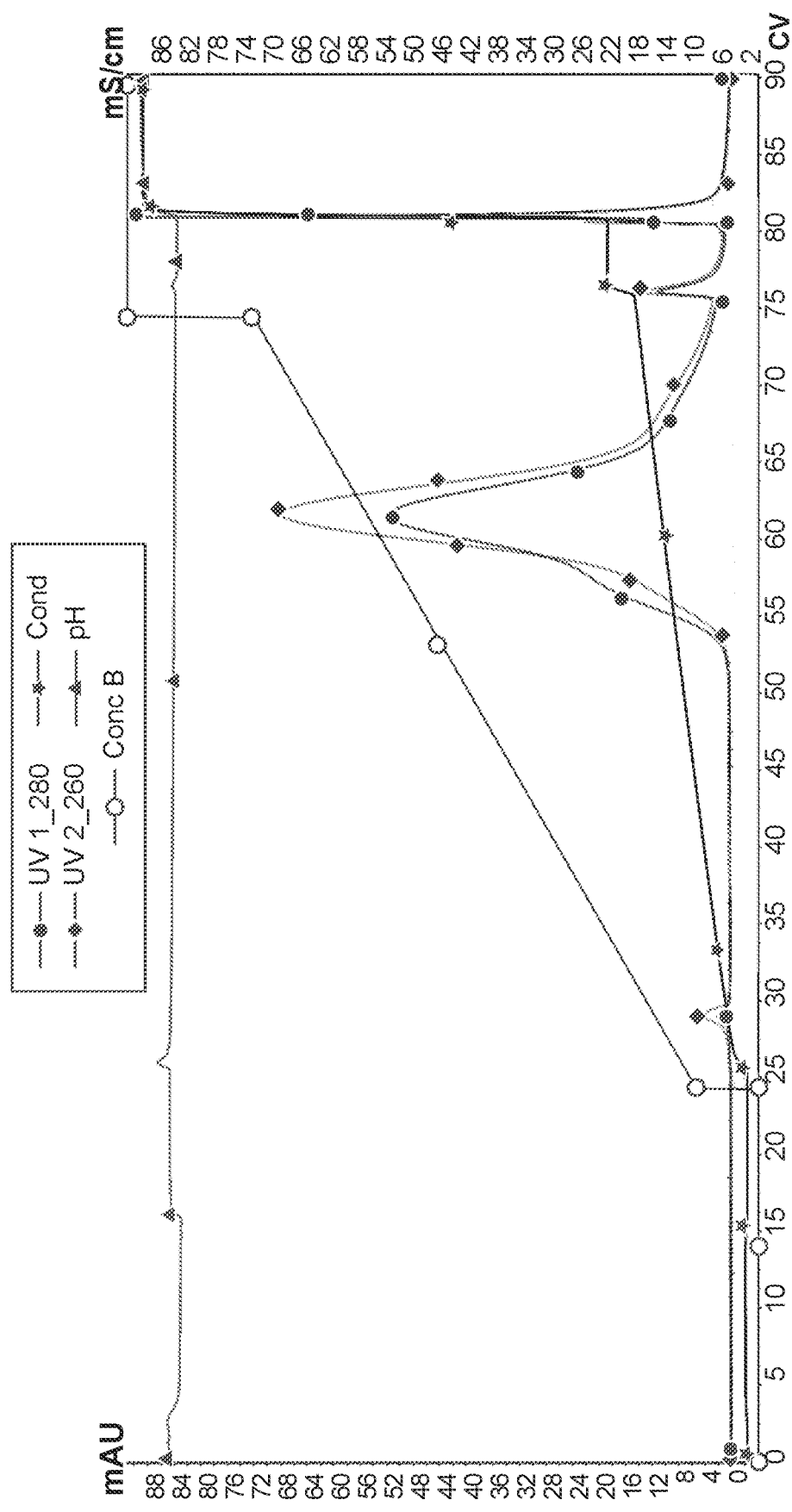

Multiple AEX resins were tested to develop a large scale, high yield purification step capable of separating rAAV particles from process related impurities, including aggregates, misfolded particles, empty capsids, and partially filled capsids. Separation of functional rAAV particles from empty/partially filled capsids and viral aggregates is particularly challenging given the high level of structural similarity among the solvent accessible outside of these entities. At the same time, separating empty and partially filled capsids from functional rAAV particles is crucial for the production of a safer and more efficacious therapeutic AAV compositions. The resins tested were CIMmultus® QA, Q Sepharose, Fractogel® TMAE (M), Toyopearl® Gigacap Q-650M, and POROS™ 50 HQ.

rAAV was produced in a HEK293 based process. rAAV comprising cell culture supernatant was harvested and clarified by depth filtration, without the use of centrifugation. The clarified culture was concentrated using tangential flow filtration, and subjected to affinity purification using POROS™ CaptureSelect™ AAV8, AAV9 or AAVX resins to isolate the rAAV particles. The affinity purified composition was used to test the AEX resins. AEX chromatography was performed according to standard protocols. Briefly, the AEX columns were loaded at a rate of approximately 0.6 L cell culture equivalent/mL AEX resin. Column volumes (CV) were 1 to mL. Tris pH 8.4 buffer was used for all phases. Loading and elution was done at a flow rates of 150 cm/hr, except that 90 cm/hr flow rate was used for Fractogel® TMAE (M), and 0.5-1.25 CV/min flow rate was used for CIMmultus® QA. The columns were eluted with a shallow linear NaCl gradient starting at 5-15 mM of NaCl and reaching 120-200 mM NaCl over 30-60 CV. Column performance was evaluated based on chromatogram and peak area analysis. Results obtained with AAV8-A virus (e.g. AAV8 carrying transgene A) are shown in FIGS. 1A-1E. CIMmultus® QA separated of rAAV particles and process related impurities (empty capsids and aggregated or misfolded particles) into multiple peaks with high resolution (FIG. 1A). Q Sepharose XL yielded low resolution of rAAV particles and impurities (FIG. 1B). It also suffered from run to run variations. Fractogel® TMAE (M) provided limited separation of full AAV8-A from product related impurities (FIG. 1C). Toyopearl® Gigacap Q-650M gave poor resolution of impurities and low yield of rAAV particles (FIG. 1D). POROS™ 50 HQ provided limited separation of full AAV8-A from product related impurities (FIG. 1E). CIMmultus® QA provided a surprisingly better separation of empty/partially filled capsids from functional rAAV particles than the other resins tested, including other chemically similar resins comprising quaternary amine ligands. Based on these results, CIMmultus® QA was elected for further testing.

Figure 2A:
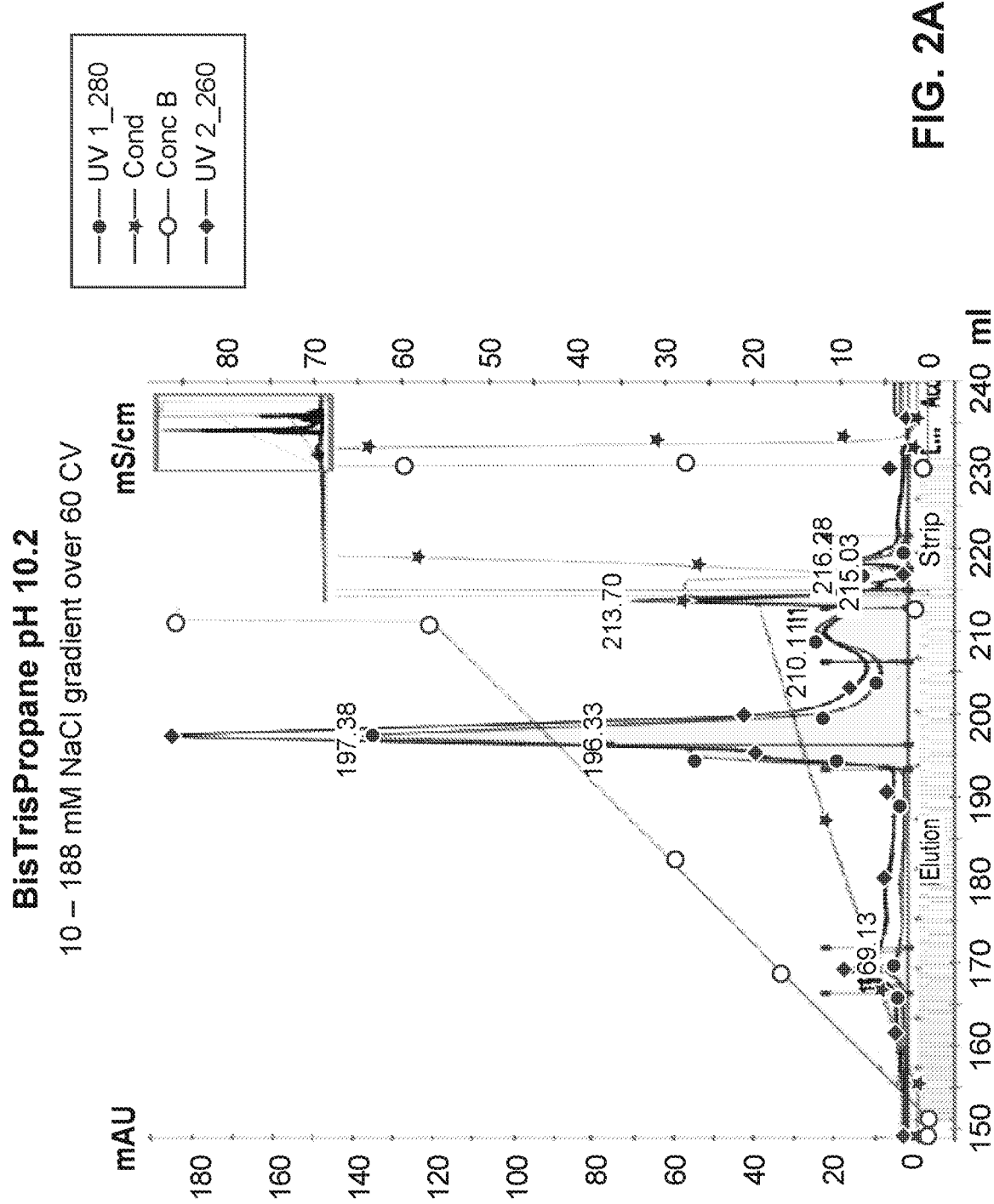
FIG. 2A-2C. Buffering agent, pH, and elution gradient impact on separation of AAV8-A full particles from product related impurities. Chromatography runs using BisTrisPropane pH 10.2 (A), Tris pH 8.8 (B) and Tris pH 8.2 (C) are shown.
Figure 2B:
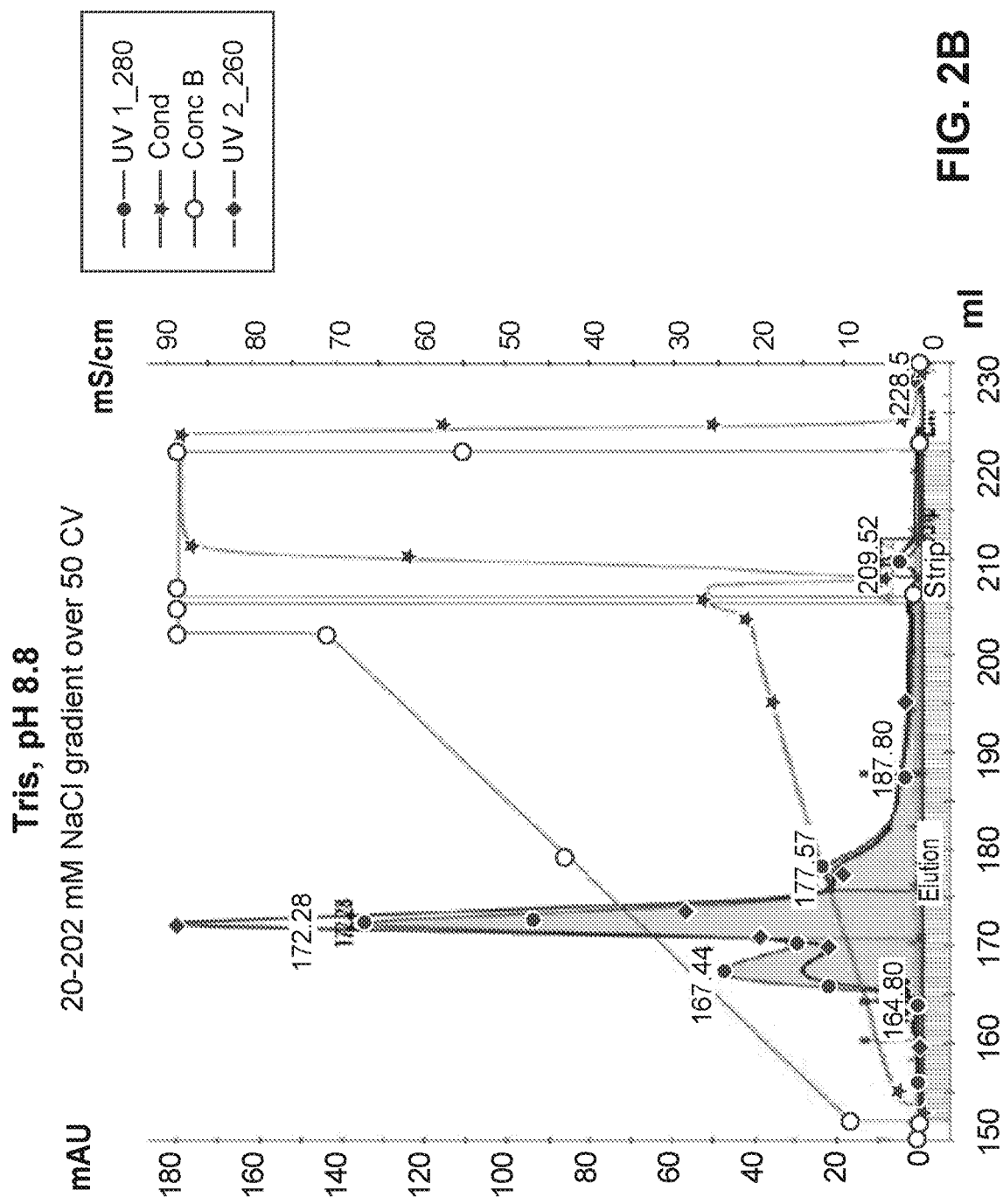
Figure 2C:
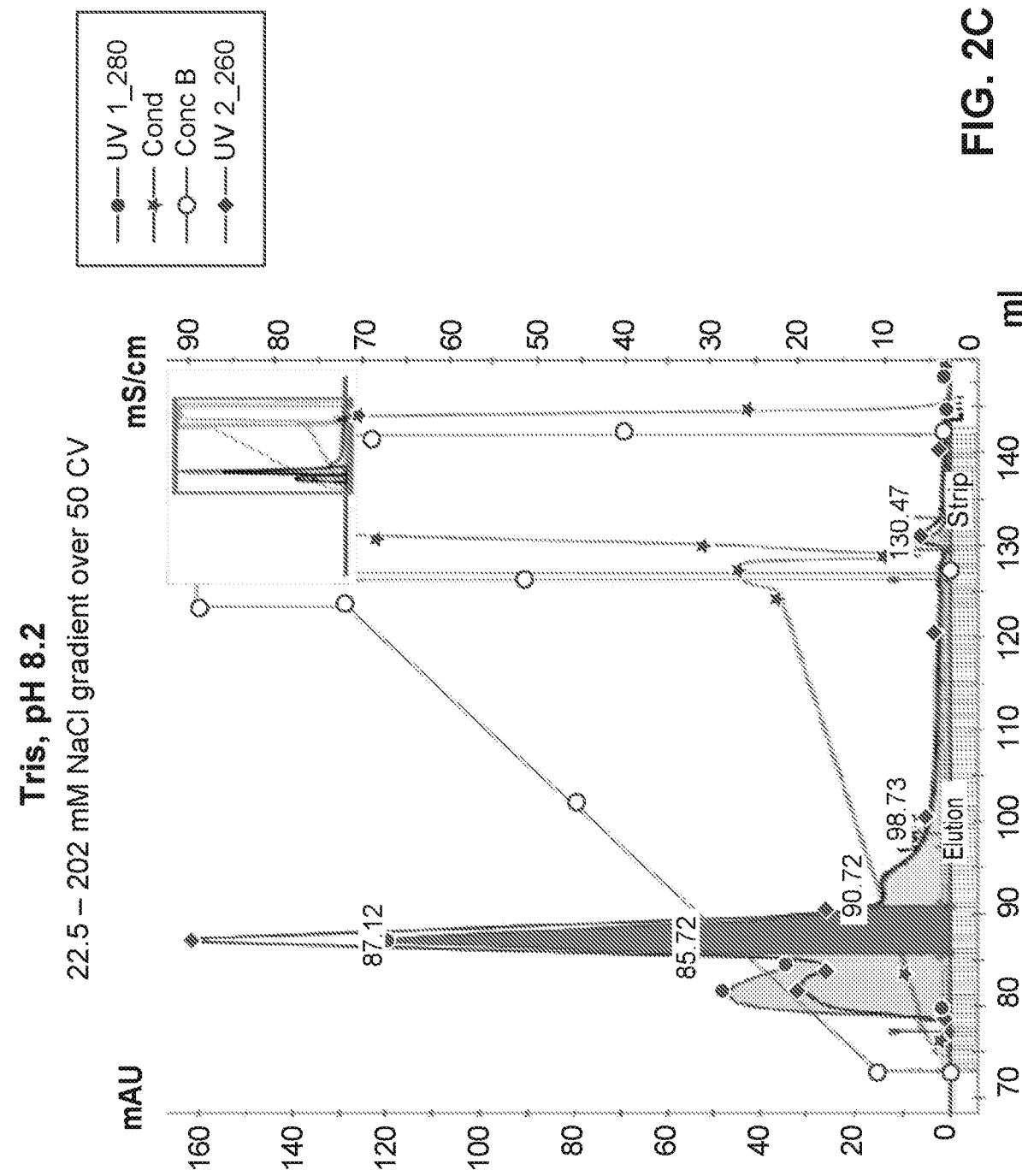

Example 2. Impact of Buffer Component, pH, and Gradient Profile on Separation of AAV8 from Product Related Impurities Further experiments were performed with affinity chromatography purified AAV8-A preparations on 1 mL CIMmultus® QA monolith columns to test the impact of buffer component, pH, and gradient profile on separation of AAV8-A from product related impurities. 25 mM Tris at pH 8.4±0.2 was optimal for chromatography buffers during the purification of AAV8-A, which ensured a tight binding of AAV8-A to the AEX media and a good separation of full AAV from product-related impurities without compromising AAV stability (FIG. 2).

Figure 3A:
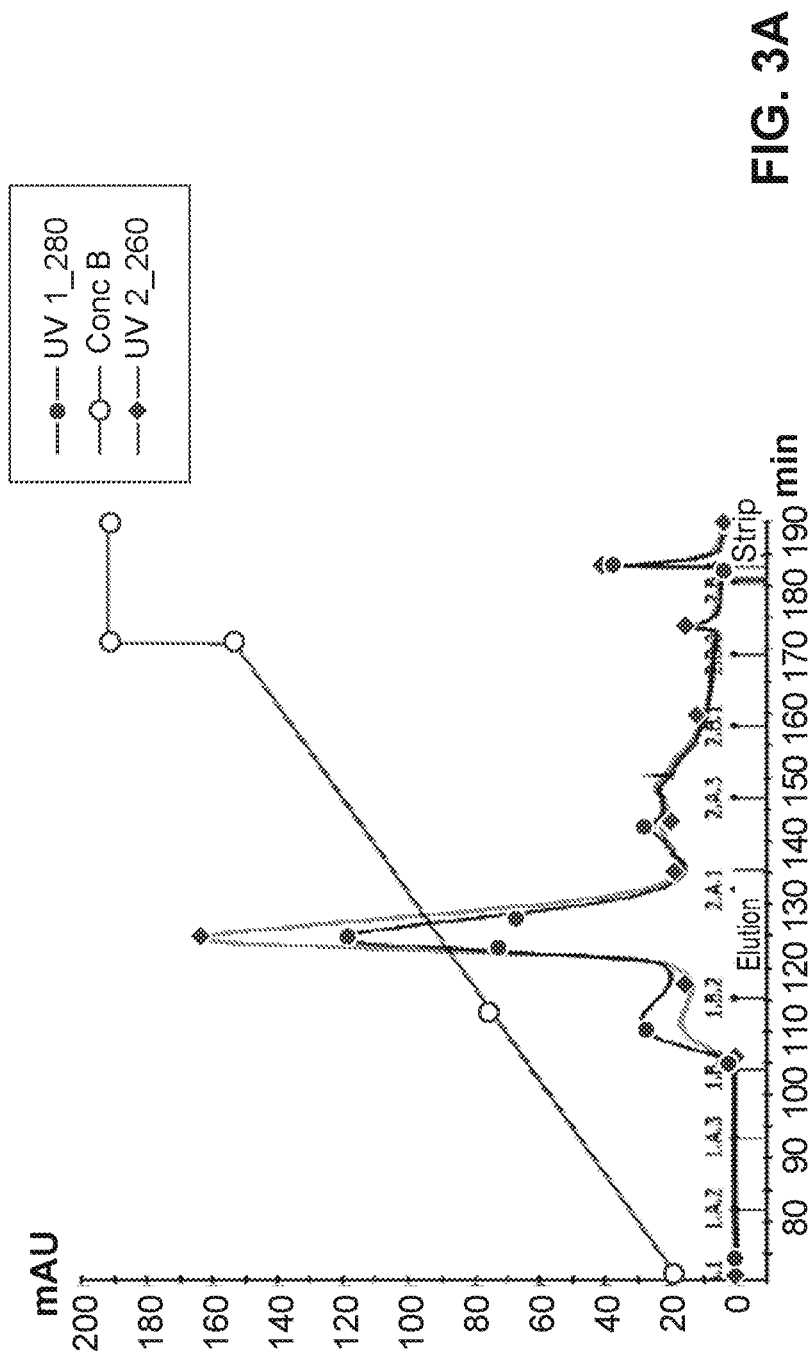
FIGS. 3A-3C. Inclusion of $Mg^{2+}$ and $K^+$ in buffers increases AEX chromatography resolution and AAV8-A yield. Chromatography runs using no $Mg^{2+}$ and $K^+$ (A), 1 mM $Mg^{2+}$ (B), and 2.5 mM $Mg^{2+}$ and 1 mM (C) are shown.
Figure 3B:
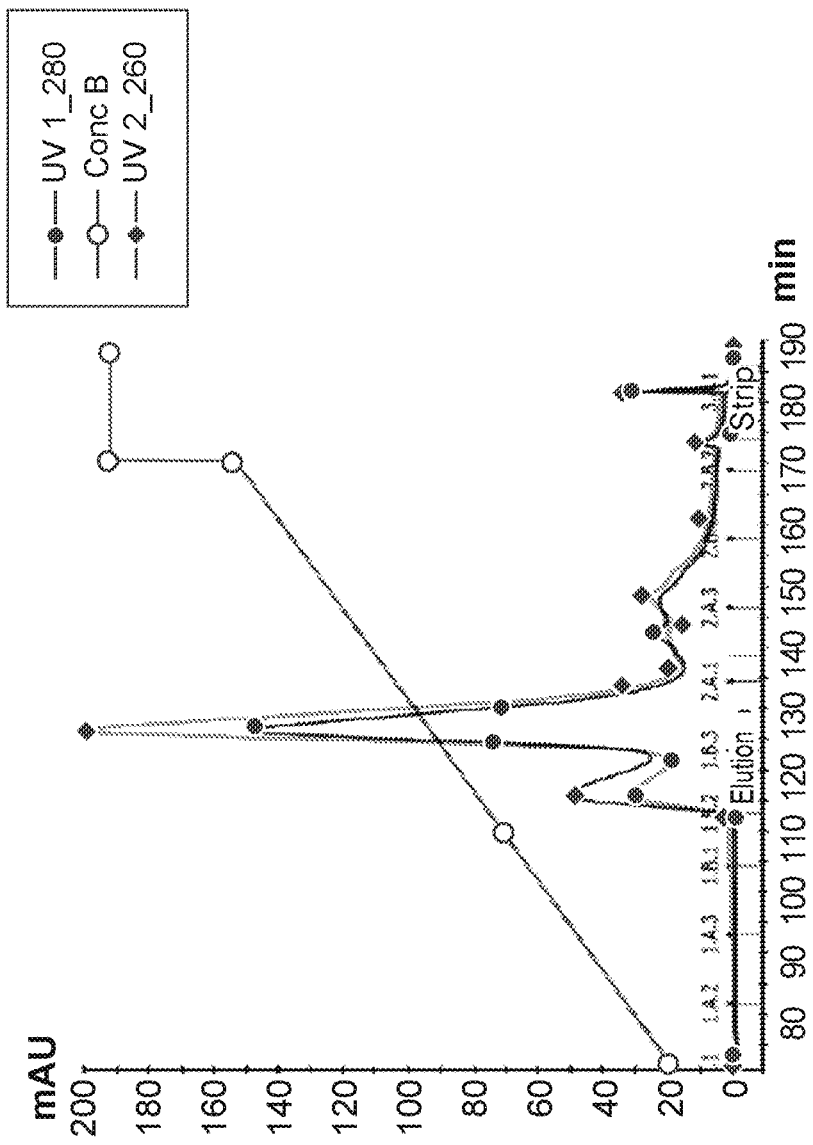
Figure 3C:
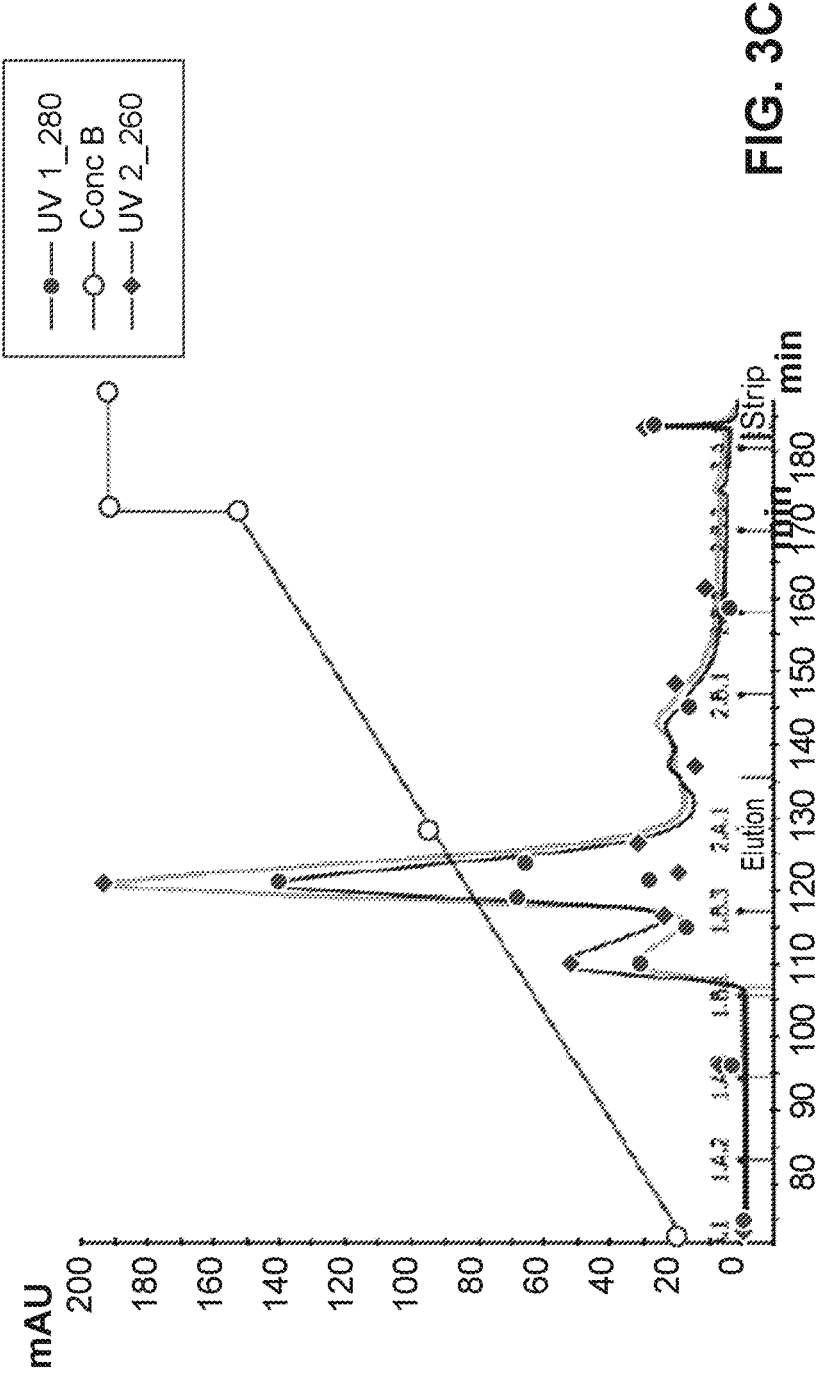

Inclusion of $MgCl_2$ and KCl in chromatography buffers increased chromatography resolution and AAV8-A yield (FIG. 3). AAV8-A, purified by affinity chromatography, was diluted with Load Dilution Buffer (25 mM Tris, 0.001% PF-68, pH 8.8) without $MgCl_2$/KCl, or with 1 mM $MgCl_2$, or with 2.5 mM $MgCl_2$ and 1 mM KCl. The Equilibration Buffer was 25 mM Tris, 5 mM NaCl pH 8.4 without $MgCl_2$/KCl, or with 1 mM $MgCl_2$, or with 2.5 mM $MgCl_2$ and 1 mM KCl and the Elution Buffer was 25 mM Tris, 200 mM NaCl pH 8.4 without $MgCl_2$/KCl, or with 1 mM $MgCl_2$, or with 2.5 mM $MgCl_2$ and 1 mM KCl. A linear NaCl concentration gradient from 19 mM NaCl to 162 mM NaCl was delivered over 60 CV to elute the column. Chromatography buffers with 1 mM $MgCl_2$ showed improved separation of full AAV8-A particles form product-related impurities. $Mg^{2+}$ improved separation both from the empty/partially filled AAV capsids in the front of the main peak, and from the aggregated/misfolded particles at the tail of the main peak. Inclusion of 2.5 mM $Mg^{2+}$ in the chromatography buffers increased AAV8-A product peak area by 13%; and increased GC step yield from 76% to 85%. Improved separation from the empty/partially filled AAV capsids is reflected in the reduced GC titer in the "Front" (1.9% vs. 1.50%). Whereas the improved separation from aggregated/misfolded particles is reflected in the reduced yield GC titer in the "Tail" (9.39% vs 4.71%). FIG. 3. In both cases, the reduced yield GC titer in the Front and Tail fractions means an increased yield GC titer in the main fraction comprising the functional rAAV particles. Introduction of $K^+$ in addition to $Mg^{2+}$ resulted in further yield improvement. Inclusion of 2.5 mM $MgCl_2$ and 1 mM KCl in the chromatography buffers increased AAV8-A product peak area by 15%; and increased GC step yield from 76% to 91%. The presence of K$^+$ further improved separation from the empty/partially filled AAV capsids as reflected by the reduced GC titer in the "Front." GC titer in the "Front" went from 1.9% without K$^+$ or Mg2$^+$ to 1.5% with Mg2$^+$ alone, and to 1.42% with K$^+$ and Mg2$^+$. Of the conditions tested, the best separation of full AAV8-A from product-related impurities, and the best product yield was achieved by using the optimal buffer system (Tris) and pH (pH 8.4), including 2.5 mM MgCl$_2$ and 1 mM KCl in chromatography running buffers, using a slower flow-rate, and applying shallow linear NaCl concentration gradient for product elution (FIG. 3 chromatography run C), when compared to buffers without any Mg$^{2+}$ or K$^+$ (FIG. 3 chromatography run A).

Figure 4B:
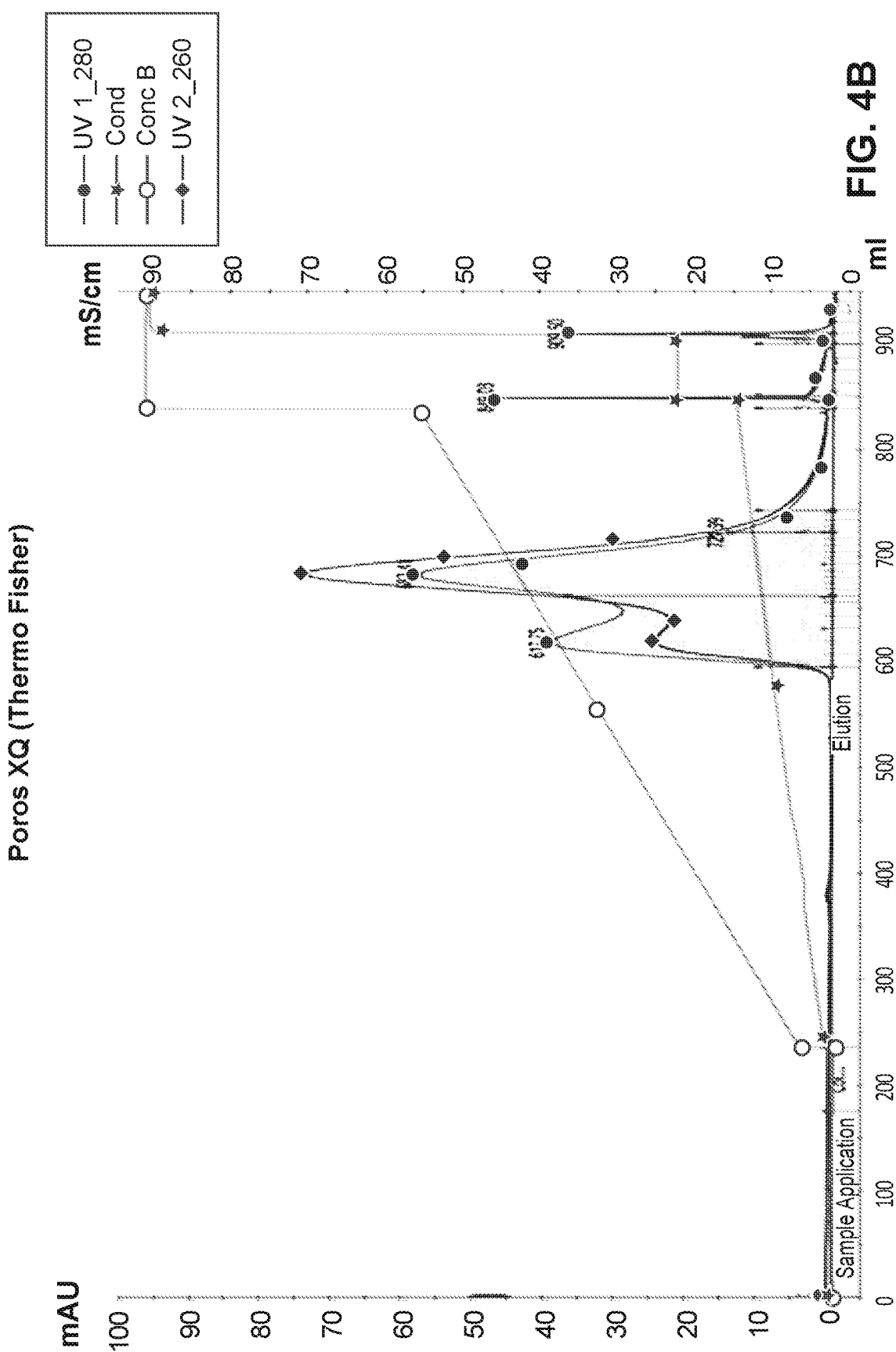
Figure 4C:
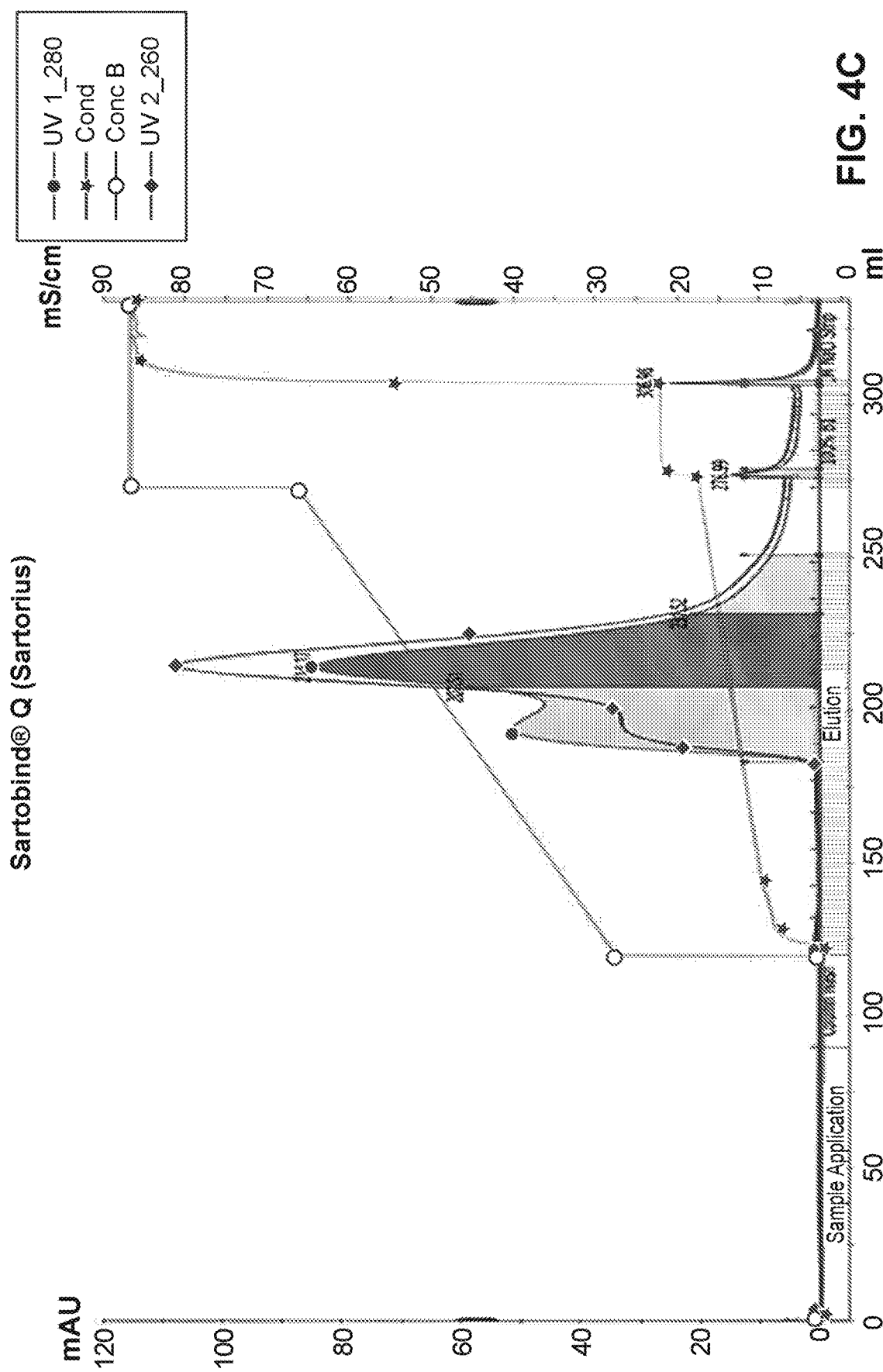

Example 3. Inclusion of Mg$^{2+}$ and K$^+$ in the Buffer System Improves Separation of Full AAV Particles from Empty/Partially Filled Capsids and Viral Aggregates in AEX Chromatography Multiple AEX chromatography resins comprising quaternary amine ligands were tested for their ability to separate full AAV particles from empty/partially filled capsids and aggregates when using a buffer system comprising Mg$^{2+}$ and K$^+$. FIG. 4. CIMmultus™ QA (BIA Separations), Poros XQ (Thermo Fisher), and Sartobind® Q (Sartorius) AEX media were used to purify AAV8-B viruses (e.g. AAV8 carrying transgene B). AAV8-B viruses were harvested from cell culture supernatant and purified on a Poros AAVX affinity column, substantially as described in Example 1. The affinity purified AAV8-B viruses were diluted with 20 mM TrisHCl Buffer (optionally containing 2 mM MgCl$_2$, 2.5 mM KCl, and 0.001% Pluronic to prevent "sticking") and loaded onto an the AEX column, which was pre-equilibrated with Equilibration/Wash Buffer (25 mM TrisHCl, 2 mM MgCl$_2$, 2.5 mM KCl pH8.4). The columns were washed with Equilibration/Wash Buffer, and subsequently eluted by a linear gradient of increasing NaCl concentration. All three resins tested provided good separation between the main peak comprising the full AAV8-B particles and the front peak comprising empty/partially filled capsids, as well as the tail comprising aggregated viruses. The separation observed for AAV8-B using a buffer system comprising Mg$^{2+}$ and K$^+$ (FIG. 4) was significantly better compared to the separation observed with quaternary amine AEX columns for AAV8-A using a buffer system that did not comprises Mg$^{2+}$ and K$^+$ (FIGS. 1A, B, D, and E).

Figure 5:
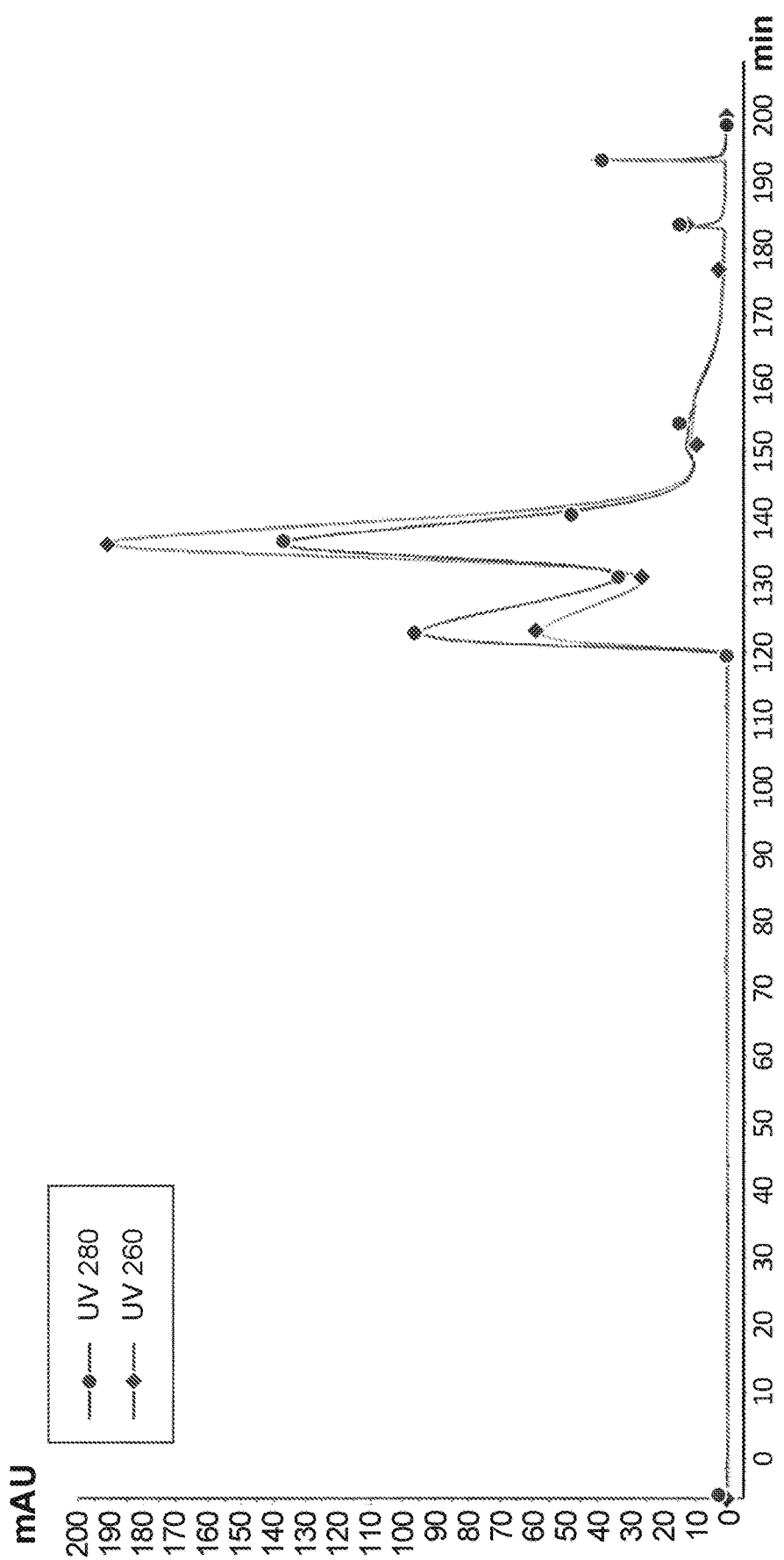
FIG. 5 AAV8-A AEX chromatography scale up to 50 L cell suspension culture using an 80 mL CIMmultus® QA column.

Example 4. Large Scale Purification of AAV8 Particles Using CIMmultus® QA AEX Chromatography AAV8-A was isolated from 50 L of cell culture supernatant as described in Example 1, and was further purified using a 80 mL CIMmultus® QA monolith column using the buffer system comprising Tris pH 8.4, 2.5 mM MgCl$_2$ and 1 mM KCl, a slow flow-rate, and a shallow linear NaCl concentration gradient as described in Example 2. The AEX chromatography method scaled up to an 80 mL CIMmultus® QA column separated affinity purified AAV8-A into three fractions or peaks: the 1$^{st}$ or front peak (in which the absorbance at 280 nm>the absorbance at 260 nm) containing empty viral capsids; the 2$^{nd}$ or major peak, (in which the absorbance at 260 nm>the absorbance at 280 nm) comprising the full AAV8-A particles and minimal product-related impurities; the 3$^{rd}$ or tail peak comprising a mixture of various product-related impurities (such as aggregated, misfolded or degraded AAV particles) (FIG. 5). The average AAV8-A genome copy (GC) yield for the CIMmultus® QA chromatography process from 6 runs was 92%.

Figure 6:
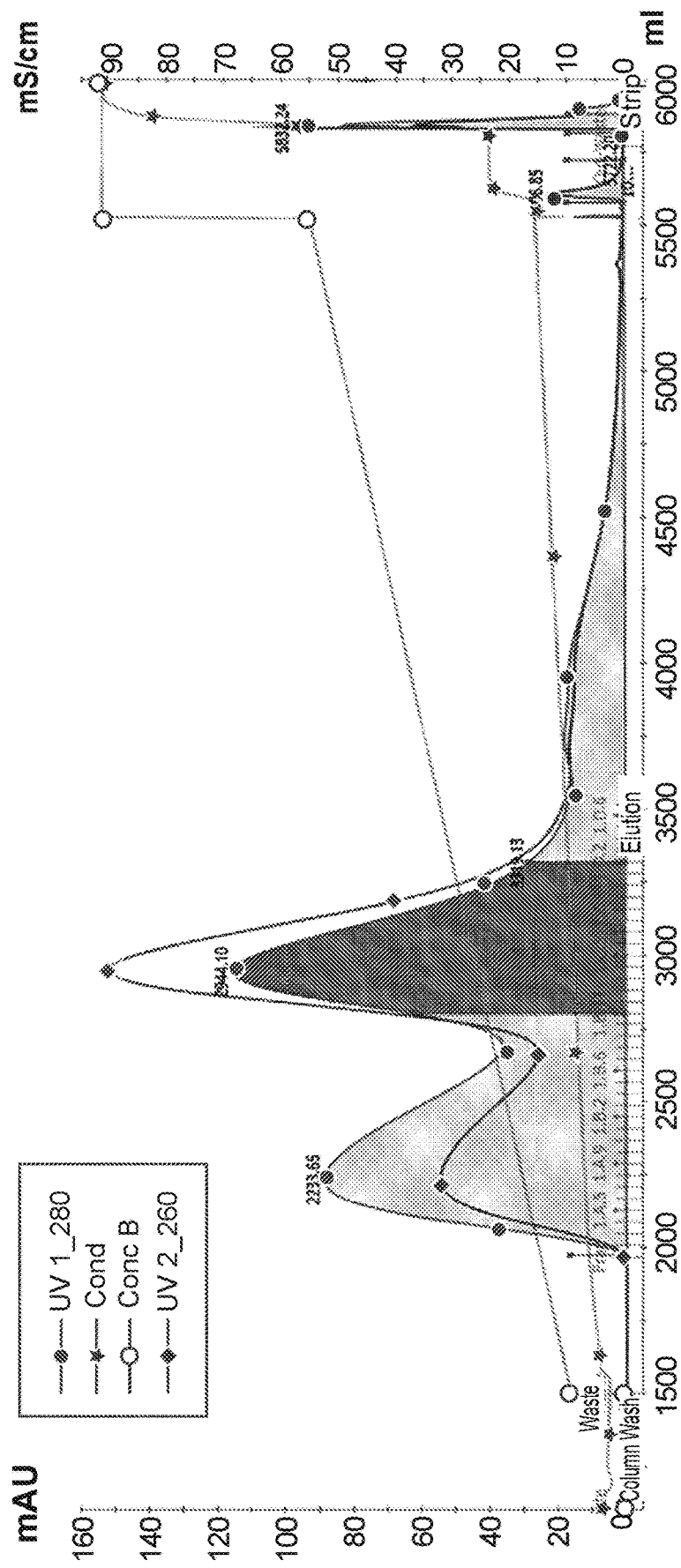
FIG. 6 AAV8-B AEX chromatography scale up to 60 L cell suspension culture using an 80 mL CIMmultus® QA column.

AAV8-B particles harvested from a 60 L suspension cell culture supernatant were purified on a Poros AAVX affinity chromatography column, substantially as described in Example 1. The affinity purified preparation was diluted 12 fold with 20 mM TrisHCl, 1 mM MgCl2, 1 mM KCl and 0.001% Pluronic pH8.8, and loaded onto an 80 mL CIM QA column pre-equilibrated by Equilibration/Wash Buffer (25 mM TrisHCl, 8.0 mM MgCl2, 2.5 mM KCl pH8.8). AAV8-B bound to the column was eluted by a linear gradient of increasing NaCl concentration. AAV8-B particles were collected based on A260 and A280 absorption values. Fractions starting at A260/A280>1.1 (front) and ending at A280 reaching 25% of Maximum Peak were pooled. FIG. 6. The pooled elution fractions were neutralized by adding 0.2M Tris-HCl, 0.01% Pluronic PF-68, pH 7.2±0.2. The CIM QA column purification had a GC yield of 77%. 78% of the isolated particles were full AAV, as indicated by analytical ultracentrifugation. The CIM QA column step eliminated 64% of the impurities, as assessed based on A280 values.

Figure 7:
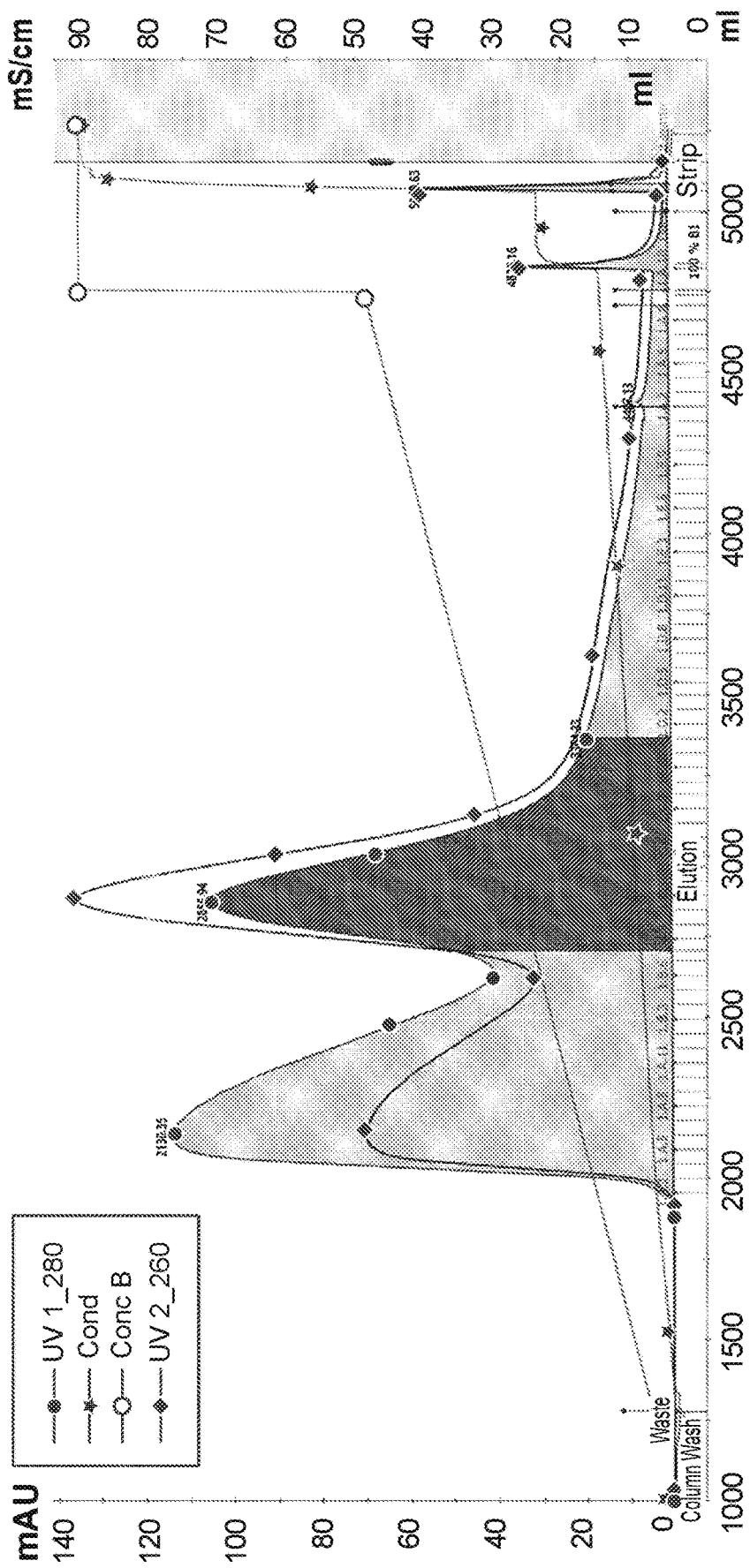
FIG. 7 AAV8-C AEX chromatography scale up to 50 L cell suspension culture using an 80 mL CIMmultus® QA column.

AAV8-C particles (e.g. AAV8 particles comprising transgene C) harvested from a 50 L suspension cell culture supernatant was purified on a Poros AAVX affinity chromatography column, substantially as described in Example 1. The affinity purified preparation was diluted 12 fold with 20 mM TrisHCl, 1 mM MgCl2, 1 mM KCl and 0.001% Pluronic pH8.8, and loaded onto an 80 mL CIM QA column pre-equilibrated by Equilibration/Wash Buffer (25 mM TrisHCl, 8.0 mM MgCl2, 2.5 mM KCl pH8.8). AAV8-B bound to the column was eluted by a linear gradient of increasing NaCl concentration. AAV8-B particles were collected based on A260 and A280 absorption values. Fractions starting at A260/A280>1.0 (front) and ending at A280 reaching 20% of Maximum Peak were pooled. FIG. 7. The pooled elution fractions were neutralized by adding 0.2M Tris-HCl, 0.01% Pluronic PF-68, pH 7.2±0.2. The CIM QA column purification had a GC yield of 100%. 51% of the isolated particles were full AAV and 30% were partial AAV, as indicated by analytical ultracentrifugation. The CIM QA column step eliminated 65% of the impurities, as assessed based on A280 values.

Example 5. AAV9 Purification by AEX Chromatography

Figure 8B:
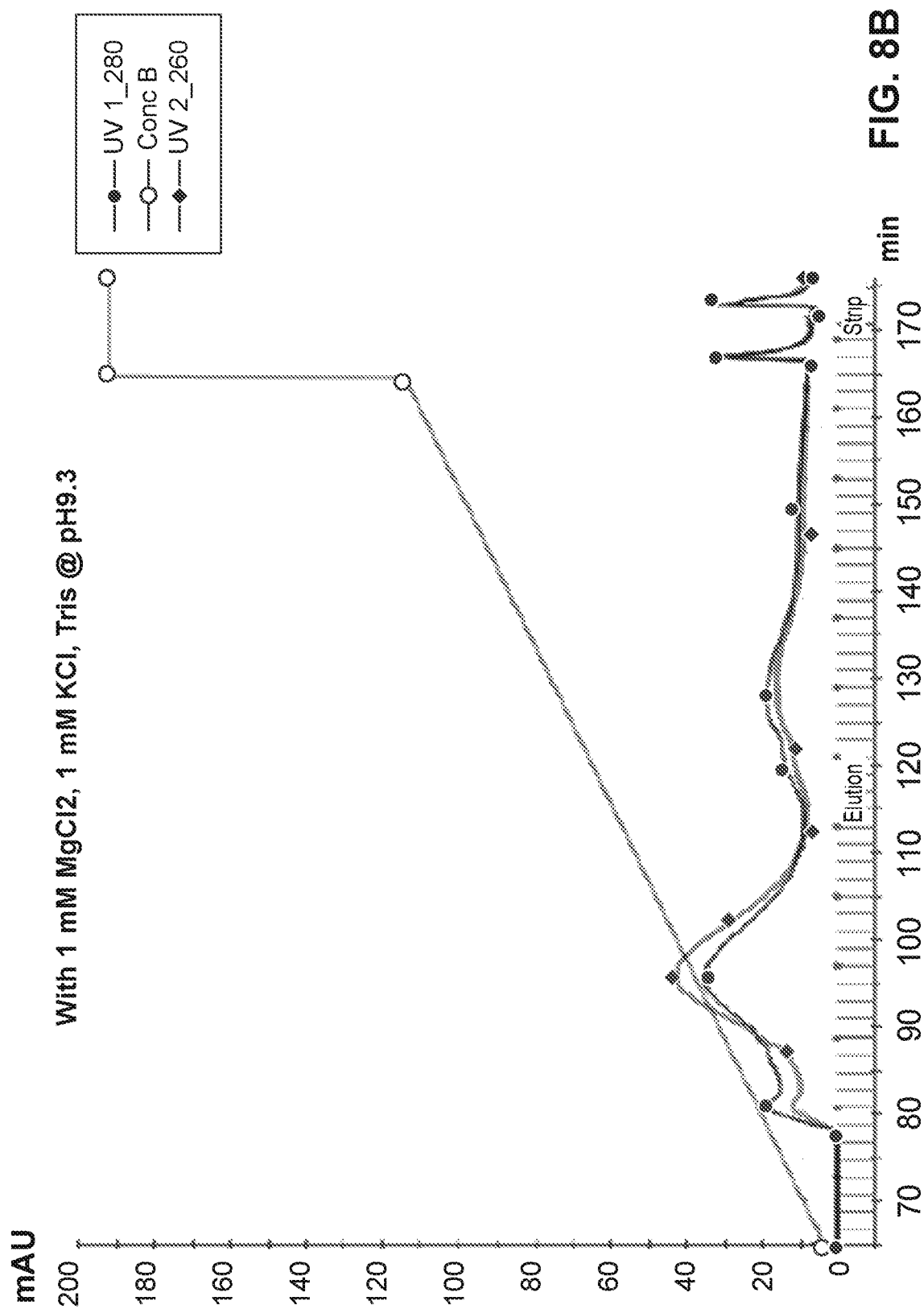

An AAV9 virus, purified by affinity chromatography using the process described in Example 1, was further purified by anion exchange chromatography using a CIMmultus® QA column. The sample was diluted with AEX Load Dilution Buffer (25 mM Tris, 0.001% PF-68, pH 10.0) with or without 1 mM MgCl$_2$ and 1 mM KCl. The Equilibration Buffer was: 25 mM Tris, 3 mM NaCl, pH 9.3, with or without 1 mM MgCl$_2$ and 1 mM KCl; and the Elution Buffer was: 25 mM Tris, 200 mM NaCl, pH 9.3 with or without 1 mM MgCl$_2$ and 1 mM KCl. A linear NaCl concentration gradient from 9 mM NaCl to 121 mM NaCl was delivered over 50 CV to elute the AAV9 particles. Inclusion of 1 mM MgCl$_2$ and 1 mM KCl in the chromatography buffers increased AAV9 product peak area by 12%; and increased GC step yield from 76% to 79% (FIG. 8).

While the disclosed methods have been described in connection with what is presently considered to be the most practical and preferred embodiments, it is to be understood that the methods encompassed by the disclosure are not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. A method for isolating recombinant adeno-associated virus (rAAV) particles from a feed composition containing rAAV particles and an impurity comprising:
    (a) contacting the feed composition with an anion exchange chromatography media under conditions that allow binding of the rAAV particles to the chromatography media;
    (b) eluting the rAAV particles from the chromatography media using a linear gradient; and
    (c) recovering an eluate comprising the eluted rAAV particles;
wherein
    (i) the impurity comprises an empty viral capsid, partially filled viral capsid, and/or a viral aggregate, and
    (ii) the method is characterized by that:
        a. the feed composition has a Mg2+ concentration of between about 0.1 mM and about 20 mM,
        b. the feed composition has a K+ concentration of between about 0.1 mM and about 20 mM, and
        c. the feed composition has a pH of between about 6.5 and about 10.5.

2. A method for improving the separation between empty or partially filled recombinant adeno-associated virus (rAAV) particles and full rAAV particles during anion exchange chromatography comprising:
    (a) contacting a feed composition containing empty, partially filled and full rAAV particles with an anion exchange chromatography media under conditions that allow binding of the rAAV particles to the chromatography media;
    (b) eluting the rAAV particles from the chromatography media using a linear gradient; and
    (c) recovering an eluate comprising the eluted rAAV particles;
wherein the method is characterized by that:
    a. the feed composition has a Mg2+ concentration of between about 0.1 mM and about 20 mM,
    b. the feed composition has a K+ concentration of between about 0.1 mM and about 20 mM, and
    c. the feed composition has a pH of between about 6.5 and about 10.5.

3. A method for improving the separation between recombinant adeno-associated virus (rAAV) particles and viral aggregates during anion exchange chromatography comprising:
    (a) contacting a feed composition containing rAAV particles and viral aggregates with an anion exchange chromatography media comprising under conditions that allow binding of the rAAV particles to the chromatography media;
    (b) eluting the rAAV particles from the chromatography media using a linear gradient; and
    (c) recovering an eluate comprising the eluted rAAV particles;
wherein the method is characterized by that:
    a. the feed composition has a Mg2+ concentration of between about 0.1 mM and about 20 mM,
    b. the feed composition has a K+ concentration of between about 0.1 mM and about 20 mM, and
    c. the feed composition has a pH of between about 6.5 and about 10.5.

4. The method of claim 3, wherein the method is characterized by that:
    a. the eluting is done at a flow rate of between 0.1 CV/min and 5 CV/min, and
    b. the linear salt gradient comprises a volume of between about 5 and about 100 CV.

5. The method of claim 3, wherein the method is characterized by that
    a. the feed composition has a Mg2+ concentration of between about 0.5 mM and about 10 mM,
    b. the feed composition has a K+ concentration of between about 0.5 mM and about 10 mM, and
    c. the feed composition has a pH of between about 6.5 and about 10.5.

6. The method of claim 3, wherein the anion exchange chromatography media comprises a quaternary amine functional group.

7. The method of claim 3, wherein the anion exchange chromatography media is a monolith anion exchange chromatography.

8. The method of claim 3, wherein the linear salt gradient comprises between about 0 and 500 mM NaCl.

9. The method of claim 3, further comprising washing the chromatography media comprising the bound rAAV particles prior to eluting, wherein the wash buffer comprises between about 0.1 mM and about 20 mM Mg2+.

10. The method of claim 3, further comprising washing the chromatography media comprising the bound rAAV particles prior to eluting, wherein the wash buffer comprises between about 0.1 mM and about 20 mM K+.

11. The method of claim 3, further comprising washing the chromatography media comprising the bound rAAV particles prior to eluting, wherein the wash buffer comprises between about 0.1 mM and about 20 mM Mg2+ and between about 0.1 mM and about 20 mM K+.

12. The method of claim 3, further comprising washing the chromatography media comprising the bound rAAV particles prior to eluting, wherein the wash buffer comprises 8 mM MgCl2 and 2.5 mM KCl.

13. The method of claim 3, wherein the anion exchange chromatography media has been equilibrated with a buffer comprising 8 mM MgCl2 and 2.5 mM KCl prior to contacting the feed composition with the anion exchange chromatography media.

* * * * *

UNITED STATES PATENT AND TRADEMARK OFFICE
CERTIFICATE OF CORRECTION

PATENT NO. : 12,070,702 B2
APPLICATION NO. : 17/251869
DATED : August 27, 2024
INVENTOR(S) : Zhang et al.

Page 1 of 1

It is certified that error appears in the above-identified patent and that said Letters Patent is hereby corrected as shown below:

On the Title Page

-Under "OTHER PUBLICATIONS," Line 7, after "Spring May 24, 2012," change "18 pages," to --48 pages,--

In the Specification

-Column 10, Lines 53-54, change "and 1 mM (A) and with 1 mM Mg2+ and 1 mM (B) are shown." to --and 1 mM K+ (A) and with 1 mM Mg2+ and 1 mM K+ (B) are shown.--
-Column 12, Line 34, change "as applied to a an AAV particle" to --as applied to an AAV particle--
-Column 12, Line 66, change "of two or more thereof)" to --of two or more thereof--
-Column 14, Line 52, change "i.e., a monoliths" to --i.e., monoliths--
-Column 22, Lines 26-28, change "In some embodiments, the feed composition comprises about 1 mM Mg2+. In some embodiments, the feed composition comprises about 1 mM Mg2+." to --In some embodiments, the feed composition comprises about 1 mM Mg2+.--
-Column 22, Line 31, change "20 mM Ca'" to --20 mM Ca2+--
-Column 22, Line 33, change "about 0.1 mM and about 20 mM" to --about 0.1 mM and about 20 mM Zn2+.--
-Column 25, Line 44, change "liner salt gradient" to --linear salt gradient--
-Column 26, Lines 34-36, change "In some embodiments, pretreating comprises adjusting pH. In some embodiments, pretreating comprises adjusting pH." to --In some embodiments, pretreating comprises adjusting pH.--
-Column 34, Line 30, change "AAV5, AA6, AAV7" to --AAV5, AAV6, AAV7--
-Column 37, Line 38, change "CHO—K1 cells," to --CHO-K1 cells,--
-Column 38, Line 40, change "not included centrifugation." to --not include centrifugation.--
-Column 39, Line 63, change "form the clarified feed" to --from the clarified feed--
-Column 41, Line 61, change "were 1 to mL." to --were 1 to ~2 mL.--
-Column 42, Line 50, change "particles form product-related" to --particles from product-related--
-Column 43, Line 34, change "an the AEX column," to --the AEX column,--

Signed and Sealed this
Third Day of December, 2024

Katherine Kelly Vidal
*Director of the United States Patent and Trademark Office*